(12) United States Patent
Lobner et al.

(10) Patent No.: US 11,666,486 B2
(45) Date of Patent: Jun. 6, 2023

(54) REMOTE INTERFACE FOR DIGITAL CONFIGURATION AND SECURITY OF SAFETY EQUIPMENT

(71) Applicant: 3M INNOVATIVE PROPERTIES COMPANY, St. Paul, MN (US)

(72) Inventors: Eric C. Lobner, Woodbury, MN (US); Kiran S. Kanukurthy, Cottage Grove, MN (US); Micayla A. Johnson, Farmington, MN (US); Susan R. Johnson, Minneapolis, MN (US); Patric Anvegård, Bredaryd (SE); Emil R. Eriksson, Falun (SE); Daniel E. G. Gullberg, Gagnef (SE); Anton P. Backlund, Gustafs (SE); Derek S. Baker, Lake Elmo, MN (US); John M. Kruse, Minneapolis, MN (US)

(73) Assignee: 3M Innovative Properties Company, St. Paul, MN (US)

(*) Notice: Subject to any disclaimer, the term of this patent is extended or adjusted under 35 U.S.C. 154(b) by 552 days.

(21) Appl. No.: 16/645,108

(22) PCT Filed: Sep. 10, 2018

(86) PCT No.: PCT/US2018/050158
§ 371 (c)(1),
(2) Date: Mar. 6, 2020

(87) PCT Pub. No.: WO2019/051349
PCT Pub. Date: Mar. 14, 2019

(65) Prior Publication Data
US 2021/0121330 A1    Apr. 29, 2021

Related U.S. Application Data

(60) Provisional application No. 62/639,958, filed on Mar. 7, 2018, provisional application No. 62/556,771, filed on Sep. 11, 2017.

(51) Int. Cl.
*G08B 13/22* (2006.01)
*G08B 21/02* (2006.01)
(Continued)

(52) U.S. Cl.
CPC .............. *A61F 9/067* (2013.01); *A42B 3/225* (2013.01); *A61F 9/061* (2013.01); *G05B 19/048* (2013.01);
(Continued)

(58) Field of Classification Search
CPC ......... G05B 19/048; G06Q 10/063114; G06Q 50/00; G08B 21/02; G08B 31/00;
(Continued)

(56) References Cited

U.S. PATENT DOCUMENTS 9,449,498 B2    9/2016  Dina
9,931,247 B2    4/2018  Huh
(Continued)

FOREIGN PATENT DOCUMENTS

RU          162541       6/2016
WO     WO 2008-144126   11/2008
(Continued)

OTHER PUBLICATIONS

Connected Solutions, Advancing the Job, [online], [retrieved from the internet on Apr. 30, 2020], <https://www.milwaukeetool.com/onekey>, 8 pages.
(Continued)

*Primary Examiner* — John A Tweel, Jr.
(74) *Attorney, Agent, or Firm* — Steven A. Bern

(57) ABSTRACT

In some examples, a system includes: a plurality of different articles of personal protection equipment (PPE) that are all controlled by a particular user, and a computing device. The computing device may include one or more computer processors configured to receive sets of data from each of the
(Continued)

different articles of PPE, wherein each set of data is based at least in part on a type of each of the different articles of PPE; generate for display a user interface that contemporaneously includes a plurality of graphical elements that are based at least in part on at least two sets of data that correspond to at least two different articles of PPE of the plurality of different articles of PPE; and in response to receiving an indication of user input that corresponds to at least one of the plurality of graphical elements, perform at least one operation.

21 Claims, 7 Drawing Sheets

(51) Int. Cl.
G05B 19/048 (2006.01)
G06Q 10/0631 (2023.01)
G06F 1/16 (2006.01)
A61F 9/06 (2006.01)
H04W 12/00 (2021.01)
H04W 12/0433 (2021.01)
H04W 12/033 (2021.01)
A42B 3/22 (2006.01)
H04L 67/12 (2022.01)
G06V 40/20 (2022.01)
G08B 31/00 (2006.01)
G06Q 50/00 (2012.01)
G16Y 20/00 (2020.01)
G16Y 10/00 (2020.01)

(52) U.S. Cl.
CPC ..... *G06F 1/163* (2013.01); *G06Q 10/063114* (2013.01); *G06Q 50/00* (2013.01); *G06V 40/20* (2022.01); *G08B 13/22* (2013.01); *G08B 21/02* (2013.01); *G08B 31/00* (2013.01); *G16Y 10/00* (2020.01); *G16Y 20/00* (2020.01); *H04L 67/12* (2013.01); *H04W 12/009* (2019.01); *H04W 12/033* (2021.01); *H04W 12/0433* (2021.01)

(58) Field of Classification Search
CPC ......... G08B 13/22; G16Y 20/00; H04W 4/38; G06F 1/163
See application file for complete search history.

(56) References Cited

U.S. PATENT DOCUMENTS

| | | | |
|---|---|---|---|
| 10,055,971 B2* | 8/2018 | M R | G08B 21/182 |
| 10,515,532 B2* | 12/2019 | Kanukurthy | G08B 25/10 |
| 10,741,052 B2* | 8/2020 | Kanukurthy | G08B 21/12 |
| 11,025,725 B2* | 6/2021 | Bahners | H04L 67/125 |
| 11,127,277 B2* | 9/2021 | Kanukurthy | G08B 21/12 |
| 2009/0006894 A1 | 1/2009 | Bellofatto | |
| 2011/0006894 A1 | 1/2011 | Witwer | |
| 2013/0282438 A1 | 10/2013 | Hunter | |
| 2014/0187159 A1 | 7/2014 | Hohndel | |
| 2015/0215749 A1* | 7/2015 | Teetzel | H04W 4/10 455/518 |
| 2016/0037563 A1 | 2/2016 | Debates | |
| 2016/0048295 A1 | 2/2016 | Mao | |
| 2017/0111893 A1 | 4/2017 | Lu | |
| 2017/0169533 A1* | 6/2017 | O'Brien | G06Q 50/04 |
| 2017/0330444 A1 | 11/2017 | Gowishankar | |
| 2019/0007540 A1* | 1/2019 | Shaik | H04M 1/6066 |

FOREIGN PATENT DOCUMENTS

| | | |
|---|---|---|
| WO | WO 2008-144384 | 11/2008 |
| WO | WO 2009-029326 | 3/2009 |
| WO | WO 2009-029347 | 3/2009 |
| WO | WO 2009-032417 | 3/2009 |
| WO | WO 2009-051896 | 4/2009 |
| WO | WO 2014-028656 | 2/2014 |
| WO | WO 2016-124549 | 8/2016 |
| WO | WO 2016-144744 | 9/2016 |
| WO | WO 2017-040393 | 3/2017 |
| WO | WO 2017-106432 | 6/2017 |
| WO | WO 2017-223476 | 12/2017 |
| WO | WO 2019-051351 | 3/2019 |

OTHER PUBLICATIONS

The Bose Connect App, [online], [retrieved from the internet on Apr. 30, 2020], <https://www.bose.com/en_us/support/article/bose-connect-app-pulse.html>, 1 page.

Tool Connect, DEWALT, [online], [retrieved from the internet on Apr. 30, 2020], <http://www.dewalt.com/en-us/jobsite-solutions/tool-connect>, 11 pages.

International Search Report for PCT International Application No. PCT/IB2018/050158, dated Nov. 30, 2018, 5 pages.

* cited by examiner

REMOTE INTERFACE FOR DIGITAL CONFIGURATION AND SECURITY OF SAFETY EQUIPMENT

RELATED APPLICATIONS

This application is a national stage filing under 35 U.S.C. 371 of PCT/US2018/050158, filed Sep. 10, 2018, which claims the benefit of U.S. Provisional Application Nos. 62/556,771 filed Sep. 11, 2017, and 62/639,958, filed Mar. 7, 2018, the disclosure of which is incorporated by reference in its/their entirety herein.

TECHNICAL FIELD

The present disclosure relates to the field of personal protective equipment. More specifically, the present disclosure relates to personal protective equipment that generate data.

BACKGROUND

When working in areas where there is known to be, or there is a potential of there being, dusts, fumes, gases, airborne contaminants, fall hazards, hearing hazards or any other hazards that are potentially hazardous or harmful to health, it is usual for a worker to use personal protective equipment, such as respirator or a clean air supply source. While a large variety of personal protective equipment are available, some commonly used devices include powered air purifying respirators (PAPR), self-contained breathing apparatuses, fall protection harnesses, ear muffs, face shields, and welding masks. For instance, a PAPR typically includes a blower system comprising a fan powered by an electric motor for delivering a forced flow of air through a tube to a head top worn by a user. A PAPR typically includes a device that draws ambient air through a filter, forces the air through a breathing tube and into a helmet or head top to provide filtered air to a user's breathing zone, around their nose or mouth. An SCBA provides clean air from a compressed air tank through a tube or hose to the interior of a head top worn by a user. In some examples, various personal protective equipment may generate various types of data.

SUMMARY

This disclosure is directed to a system that implements techniques for establishing wireless connections between a computing device and multiple articles of PPE controlled by a single user to configure, and in some cases, secure such particular articles of PPE. In some instances, a worker may be assigned or otherwise control multiple different articles of PPE to protect the worker against various hazards. Certain PPE may include sensors and communication devices that provide data to a computing device assigned or otherwise controlled by the user, which may be referred to as connected PPE. Users and owners of such PPE may face various challenges associated with the use of multiple, connected articles of PPE. Such challenges may include, but are not limited to, theft or loss of the PPE, configuring multiple different articles of PPE in an efficient manner that accommodates unique user experience challenges in a work environment (e.g., wearing gloves or other heavy garments while configuring the connected PPE or operating in a high-noise environment), and displaying information and configuration options for multiple different articles of PPE in visual arrangement that enables a user to efficiently utilize and respond to data to improve worker safety. Rather than configuring each different connected article of PPE with a different user application in a set of disparate user applications, techniques of this disclosure enable a set of connected articles of PPE to each connect to a single application that provides for visualization and configuration of each article of PPE. In this way, data from multiple articles of connected PPE may be presented contemporaneously as integrated visualizations of the data that enable a user to quickly assess safety events for any of the articles of PPE that are controlled by the user. Accordingly, a user may not be required to switch between multiple different user applications executing on a computing device to view information of different articles of PPE. As such, techniques of this disclosure may reduce the time and effort of a user to identify safety events across multiple different articles of PPE assigned or controlled by a user, and therefore improve worker safety through quicker identification of such safety events than conventional techniques.

In some examples, techniques of this disclosure may provide anti-theft and loss prevention operations to locate connected PPE or prevent operations of such PPE to discourage theft. Because connected PPE may store data that could be compromised or misused in the event of theft or loss, the theft and loss-prevention operations described in this disclosure may improve the security of such connected PPE and systems using such connected PPE. In some examples, techniques of this disclosure may enable the use of particular gestures and/or voice inputs to change the configuration of one or more articles of PPE in order to accommodate user inputs that are more conductive to certain work environment (e.g., wearing gloves or other heavy garments while configuring the connected PPE or operating in a high-noise environment).

In some examples, a system may include a plurality of different articles of personal protection equipment (PPE) that are all controlled by a particular user, wherein each respective article of PPE comprises a respective communication device; a computing device comprising: a second communication device; one or more computer processors; and a memory comprising instructions that when executed by the one or more computer processors cause the one or more computer processors to: receive sets of data from each of the different articles of PPE, wherein each set of data is based at least in part on a type of each of the different articles of PPE; generate for display a user interface that contemporaneously includes a plurality of graphical elements that are based at least in part on at least two sets of data that correspond to at least two different articles of PPE of the plurality of different articles of PPE; and in response to receiving an indication of user input that corresponds to at least one of the plurality of graphical elements, perform at least one operation.

In some examples, a method may include receiving sets of data from each different article of personal protection equipment (PPE) of a plurality of different articles of PPE that are all controlled by a particular user, wherein each set of data is based at least in part on a type of each of the different articles of PPE; generating, by a computing device and for display, a user interface that contemporaneously includes a plurality of graphical elements that are based at least in part on at least two sets of data that correspond to at least two different articles of PPE of the plurality of different articles of PPE; and in response to receiving an indication of user input that corresponds to at least one of the plurality of graphical elements, performing at least one operation.

The details of one or more examples of the disclosure are set forth in the accompanying drawings and the description below. Other features, objects, and advantages of the disclosure will be apparent from the description and drawings, and from the claims.

Figure 1:
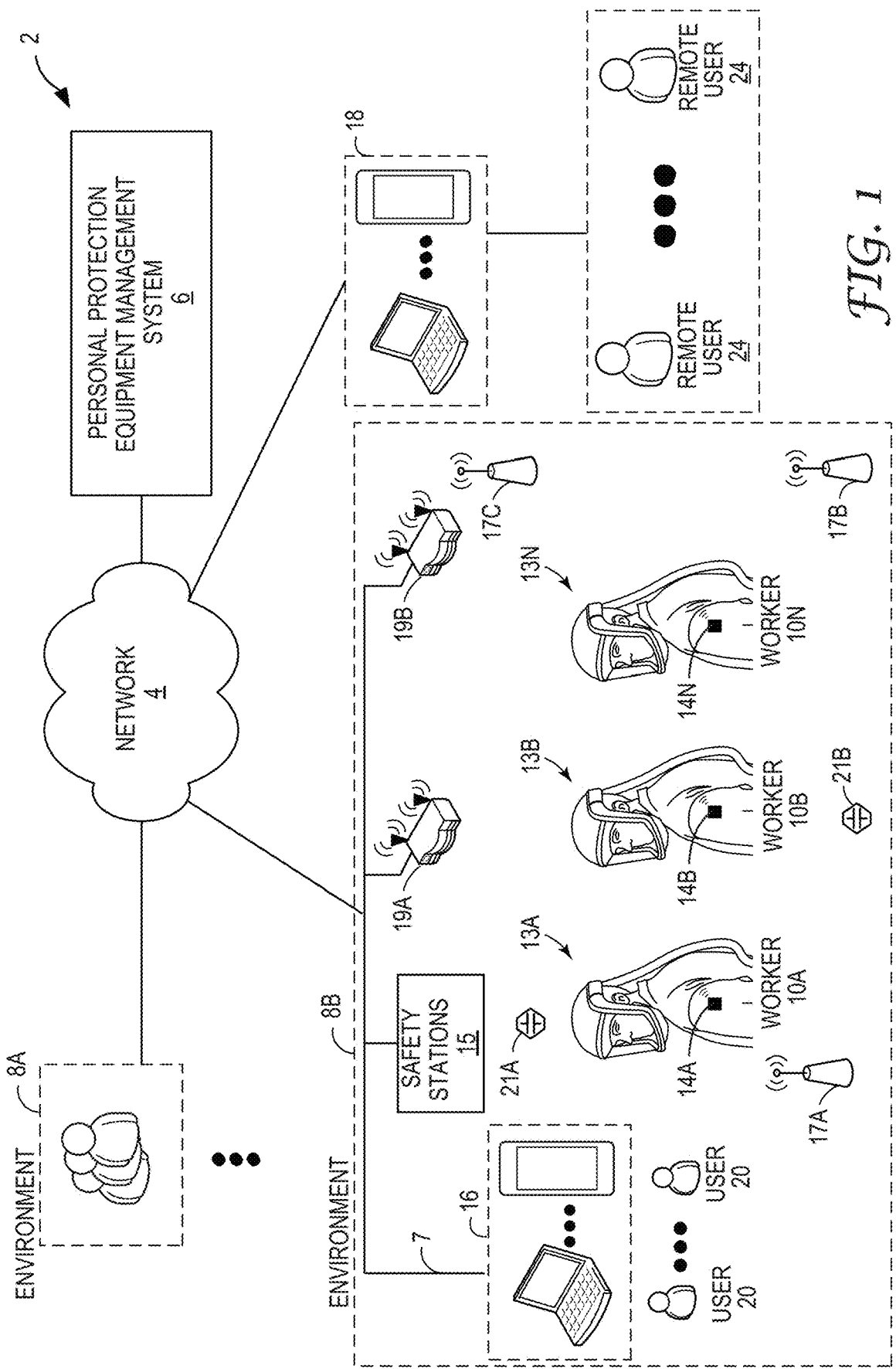
FIG. 1 is a block diagram illustrating an example system in which personal protection equipment (PPEs), such as filtered air respirator systems, having embedded sensors and communication capabilities are utilized within a number of work environments and are managed by a personal protection equipment management system (PPEMS) in accordance with various techniques of this disclosure.

It is to be understood that the embodiments may be utilized and structural changes may be made without departing from the scope of the invention. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

According to aspects of this disclosure, an article of PPE may include sensors for capturing data that is indicative of operation, location, or environmental conditions surrounding an article of PPE. Sensors may include any device that generates data or context information. Such data may generally be referred to herein as usage data or, alternatively, operation data or sensor data. In some examples, usage data may take the form of a stream of samples over a period of time. In some instances, the sensors may be configured to measure operating characteristics of components of the article of PPE, characteristics of a worker using or wearing the article of PPE, and/or environmental factors associated with an environment in which the article of PPE is located. Moreover, as described herein, the article of PPE may be configured to include one or more electronic components for outputting communication to the respective worker, such as speakers, vibration devices, LEDs, buzzers or other devices for outputting alerts, audio messages, sounds, indicators and the like.

According to aspects of this disclosure, articles of PPE may be configured to transmit the acquired usage data to a personal protection equipment management system (PPEMS), which may be a cloud-based system having an analytics engine configured to process streams of incoming usage data from personal protection equipment deployed and used by a population of workers at various work environments. The analytics engine of the PPEMS may apply the streams of incoming usage data (or at least a subset of the usage data) to one or more models to monitor and predict the likelihood of an occurrence of a safety event for the worker associated with any individual article of PPE. For example, the analytics engine may compare measured parameters (e.g., as measured by the electronic sensors) to known models that characterize activity of a user of an article of PPE, e.g., that represent safe activities, unsafe activities, or activities of concern (which may typically occur prior to unsafe activities) in order to determine the probability of an event occurring.

The analytics engine may generate an output in response to predicting the likelihood of the occurrence of a safety event. For example, the analytics engine may generate an output that indicates a safety event is likely to occur based on data collected from a user of an article of PPE. The output may be used to alert the user of the article of PPE that the safety event is likely to occur, allowing the user to alter their behavior. In other examples, circuitry embedded within the respirators or processors within intermediate data hubs more local to the workers may be programmed via the PPEMS or other mechanism to apply models or rule sets determined by the PPEMS so as to locally generate and output alerts or other preventative measure designed to avoid or mitigate a predicted safety event. In this way, the techniques provide tools to accurately measure and/or monitor operation of a respirator and determine predictive outcomes based on the operation. Although certain examples of this disclosure are provided with respect to certain types of PPE for illustration purposes, the systems, techniques, and devices of this disclosure are applicable to any type of PPE.

FIG. 1 is a block diagram illustrating an example computing system 2 that includes a personal protection equipment management system (PPEMS) 6 for managing personal protection equipment. As described herein, PPEMS allows authorized users to perform preventive occupational health and safety actions and manage inspections and maintenance of safety protective equipment. By interacting with PPEMS 6, safety professionals can, for example, manage area inspections, worker inspections, worker health and safety compliance training.

In general, PPEMS 6 provides data acquisition, monitoring, activity logging, reporting, predictive analytics, PPE control, and alert generation. For example, PPEMS 6 includes an underlying analytics and safety event prediction engine and alerting system in accordance with various examples described herein. In general, a safety event may refer to activities of a user of personal protective equipment (PPE), a condition of the PPE, or an environmental condition (e.g., which may be hazardous). In some examples, a safety event may be an injury or worker condition, workplace harm, or regulatory violation. For example, in the context of fall protection equipment, a safety event may be misuse of the fall protection equipment, a user of the fall equipment experiencing a fall, or a failure of the fall protection equipment. In the context of a respirator, a safety event may be misuse of the respirator, a user of the respirator not receiving an appropriate quality and/or quantity of air, or failure of the respirator. A safety event may also be associated with a hazard in the environment in which the PPE is located. In some examples, occurrence of a safety event associated with the article of PPE may include a safety event in the environment in which the PPE is used or a safety event associated with a worker using the article of PPE. In some examples, a safety event may be an indication that PPE, a worker, and/or a worker environment are operating, in use, or acting in a way that is normal operation, where normal operation is a predetermined or predefined condition of acceptable or safe operation, use, or activity.

As further described below, PPEMS 6 provides an integrated suite of personal safety protection equipment management tools and implements various techniques of this disclosure. That is, PPEMS 6 provides an integrated, end-to-end system for managing personal protection equipment, e.g., safety equipment, used by workers 10 within one or more physical environments 8, which may be construction sites, mining or manufacturing sites or any physical environment. The techniques of this disclosure may be realized within various parts of computing environment 2.

As shown in the example of FIG. 1, system 2 represents a computing environment in which a computing device within of a plurality of physical environments 8A, 8B (collectively, environments 8) electronically communicate with PPEMS 6 via one or more computer networks 4. Each of physical environment 8 represents a physical environment, such as a work environment, in which one or more individuals, such as workers 10, utilize personal protection equipment while engaging in tasks or activities within the respective environment.

In this example, environment 8A is shown as generally as having workers 10A-10N, while environment 8B is shown in expanded form to provide a more detailed example. In the example of FIG. 1, a plurality of workers 10A-10N are shown as utilizing respective respirators 13A-13N.

As further described herein, each of respirators 13 includes embedded sensors or monitoring devices and processing electronics configured to capture data in real-time as a user (e.g., worker) engages in activities while wearing the respirators. For example, as described in greater detail herein, respirators 13 may include a number of components (e.g., a head top, a blower, a filter, and the like) and may include a number of sensors for sensing or controlling the operation of such components. A head top may include, as examples, a head top visor position sensor, a head top temperature sensor, a head top motion sensor, a head top impact detection sensor, a head top position sensor, a head top battery level sensor, a head top head detection sensor, an ambient noise sensor, or the like. A blower may include, as examples, a blower state sensor, a blower pressure sensor, a blower run time sensor, a blower temperature sensor, a blower battery sensor, a blower motion sensor, a blower impact detection sensor, a blower position sensor, or the like. A filter may include, as examples, a filter presence sensor, a filter type sensor, or the like. Each of the above-noted sensors may generate usage data, as described herein.

In addition, each of respirators 13 may include one or more output devices for outputting data that is indicative of operation of respirators 13 and/or generating and outputting communications to the respective worker 10. For example, respirators 13 may include one or more devices to generate audible feedback (e.g., one or more speakers), visual feedback (e.g., one or more displays, light emitting diodes (LEDs) or the like), or tactile feedback (e.g., a device that vibrates or provides other haptic feedback).

In general, each of environments 8 include computing facilities (e.g., a local area network) by which respirators 13 are able to communicate with PPEMS 6. For example, environments 8 may be configured with wireless technology, such as 802.11 wireless networks, 802.15 ZigBee networks, and the like. In the example of FIG. 1, environment 8B includes a local network 7 that provides a packet-based transport medium for communicating with PPEMS 6 via network 4. In addition, environment 8B includes a plurality of wireless access points 19A, 19B that may be geographically distributed throughout the environment to provide support for wireless communications throughout the work environment.

Each of respirators 13 is configured to communicate data, such as sensed motions, events and conditions, via wireless communications, such as via 802.11 WiFi protocols, Bluetooth protocol or the like. Respirators 13 may, for example, communicate directly with a wireless access point 19. As another example, each worker 10 may be equipped with a respective one of wearable communication hubs 14A-14N that enable and facilitate communication between respirators 13 and PPEMS 6. For example, respirators 13 as well as other PPEs (such as fall protection equipment, hearing protection, hardhats, or other equipment) for the respective worker 10 may communicate with a respective communication hub 14 via Bluetooth or other short range protocol, and the communication hubs may communicate with PPEMs 6 via wireless communications processed by wireless access points 19. Although shown as wearable devices, hubs 14 may be implemented as stand-alone devices deployed within environment 8B. In some examples, hubs 14 may be articles of PPE. In some examples, communication hubs 14 may be an intrinsically safe computing device, smartphone, wrist- or head-wearable computing device, or any other computing device.

In general, each of hubs 14 operates as a wireless device for respirators 13 relaying communications to and from respirators 13, and may be capable of buffering usage data in case communication is lost with PPEMS 6. Moreover, each of hubs 14 is programmable via PPEMS 6 so that local alert rules may be installed and executed without requiring a connection to the cloud. As such, each of hubs 14 provides a relay of streams of usage data from respirators 13 and/or other PPEs within the respective environment, and provides a local computing environment for localized alerting based on streams of events in the event communication with PPEMS 6 is lost.

As shown in the example of FIG. 1, an environment, such as environment 8B, may also include one or more wireless-enabled beacons, such as beacons 17A-17C, that provide accurate location information within the work environment. For example, beacons 17A-17C may be GPS-enabled such that a controller within the respective beacon may be able to precisely determine the position of the respective beacon. Based on wireless communications with one or more of beacons 17, a given respirator 13 or communication hub 14 worn by a worker 10 is configured to determine the location of the worker within work environment 8B. In this way, event data (e.g., usage data) reported to PPEMS 6 may be stamped with positional information to aid analysis, reporting and analytics performed by the PPEMS.

In addition, an environment, such as environment 8B, may also include one or more wireless-enabled sensing stations, such as sensing stations 21A, 21B. Each sensing station 21 includes one or more sensors and a controller configured to output data indicative of sensed environmental conditions. Moreover, sensing stations 21 may be positioned within respective geographic regions of environment 8B or otherwise interact with beacons 17 to determine respective positions and include such positional information when reporting environmental data to PPEMS 6. As such, PPEMS 6 may be configured to correlate the sensed environmental conditions with the particular regions and, therefore, may utilize the captured environmental data when processing event data received from respirators 13. For example, PPEMS 6 may utilize the environmental data to aid generating alerts or other instructions for respirators 13 and for performing predictive analytics, such as determining any correlations between certain environmental conditions (e.g., heat, humidity, visibility) with abnormal worker behavior or increased safety events. As such, PPEMS 6 may utilize current environmental conditions to aid prediction and avoidance of imminent safety events. Example environmental conditions that may be sensed by sensing stations 21 include but are not limited to temperature, humidity, presence of gas, pressure, visibility, wind and the like.

In example implementations, an environment, such as environment 8B, may also include one or more safety stations 15 distributed throughout the environment to provide viewing stations for accessing respirators 13. Safety stations 15 may allow one of workers 10 to check out respirators 13 and/or other safety equipment, verify that safety equipment is appropriate for a particular one of environments 8, and/or exchange data. For example, safety stations 15 may transmit alert rules, software updates, or firmware updates to respirators 13 or other equipment. Safety stations 15 may also receive data cached on respirators 13, hubs 14, and/or other safety equipment. That is, while respirators 13 (and/or data hubs 14) may typically transmit usage data from sensors of respirators 13 to network 4 in real time or near real time, in some instances, respirators 13 (and/or data hubs 14) may not have connectivity to network 4. In such instances, respirators 13 (and/or data hubs 14) may store usage data locally and transmit the usage data to safety stations 15 upon being in proximity with safety stations 15. Safety stations 15 may then upload the data from respirators 13 and connect to network 4. a In some examples, a data hub may be an article of PPE. In some examples, a data hub may be an article of PPE.

In addition, each of environments 8 include computing facilities that provide an operating environment for end-user computing devices 16 for interacting with PPEMS 6 via network 4. For example, each of environments 8 typically includes one or more safety managers responsible for overseeing safety compliance within the environment. In general, each user 20 interacts with computing devices 16 to access PPEMS 6. Each of environments 8 may include systems. Similarly, remote users may use computing devices 18 to interact with PPEMS via network 4. For purposes of example, the end-user computing devices 16 may be laptops, desktop computers, mobile devices such as tablets or so-called smart phones and the like.

Users 20, 24 interact with PPEMS 6 to control and actively manage many aspects of safety equipment utilized by workers 10, such as accessing and viewing usage records, analytics and reporting. For example, users 20, 24 may review usage information acquired and stored by PPEMS 6, where the usage information may include data specifying starting and ending times over a time duration (e.g., a day, a week, or the like), data collected during particular events, such as lifts of a visor of respirators 13, removal of respirators 13 from a head of workers 10, changes to operating parameters of respirators 13, status changes to components of respirators 13 (e.g., a low battery event), motion of workers 10, detected impacts to respirators 13 or hubs 14, sensed data acquired from the user, environment data, and the like. In addition, users 20, 24 may interact with PPEMS 6 to perform asset tracking and to schedule maintenance events for individual pieces of safety equipment, e.g., respirators 13, to ensure compliance with any procedures or regulations. PPEMS 6 may allow users 20, 24 to create and complete digital checklists with respect to the maintenance procedures and to synchronize any results of the procedures from computing devices 16, 18 to PPEMS 6.

Further, as described herein, PPEMS 6 integrates an event processing platform configured to process thousand or even millions of concurrent streams of events from digitally enabled PPEs, such as respirators 13. An underlying analytics engine of PPEMS 6 applies historical data and models to the inbound streams to compute assertions, such as identified anomalies or predicted occurrences of safety events based on conditions or behavior patterns of workers 10. Further, PPEMS 6 provides real-time alerting and reporting to notify workers 10 and/or users 20, 24 of any predicted events, anomalies, trends, and the like.

The analytics engine of PPEMS 6 may, in some examples, apply analytics to identify relationships or correlations between sensed worker data, environmental conditions, geographic regions and other factors and analyze the impact on safety events. PPEMS 6 may determine, based on the data acquired across populations of workers 10, which particular activities, possibly within certain geographic region, lead to, or are predicted to lead to, unusually high occurrences of safety events.

In this way, PPEMS 6 tightly integrates comprehensive tools for managing personal protection equipment with an underlying analytics engine and communication system to provide data acquisition, monitoring, activity logging, reporting, behavior analytics and alert generation. Moreover, PPEMS 6 provides a communication system for operation and utilization by and between the various elements of system 2. Users 20, 24 may access PPEMS 6 to view results on any analytics performed by PPEMS 6 on data acquired from workers 10. In some examples, PPEMS 6 may present a web-based interface via a web server (e.g., an HTTP server) or client-side applications may be deployed for devices of computing devices 16, 18 used by users 20, 24, such as desktop computers, laptop computers, mobile devices such as smartphones and tablets, or the like.

In some examples, PPEMS 6 may provide a database query engine for directly querying PPEMS 6 to view acquired safety information, compliance information and any results of the analytic engine, e.g., by the way of dashboards, alert notifications, reports and the like. That is, users 24, or software executing on computing devices 16, 18, may submit queries to PPEMS 6 and receive data corresponding to the queries for presentation in the form of one or more reports or dashboards. Such dashboards may provide various insights regarding system 2, such as baseline ("normal") operation across worker populations, identifications of any anomalous workers engaging in abnormal activities that may potentially expose the worker to risks, identifications of any geographic regions within environments 2 for which unusually anomalous (e.g., high) safety events have been or are predicted to occur, identifications of any of environments 2 exhibiting anomalous occurrences of safety events relative to other environments, and the like.

As illustrated in detail below, PPEMS 6 may simplify workflows for individuals charged with monitoring and ensure safety compliance for an entity or environment. That is, the techniques of this disclosure may enable active safety management and allow an organization to take preventative or correction actions with respect to certain regions within environments 8, particular pieces of safety equipment or individual workers 10, define and may further allow the entity to implement workflow procedures that are data-driven by an underlying analytical engine.

As one example, the underlying analytical engine of PPEMS 6 may be configured to compute and present customer-defined metrics for worker populations within a given environment 8 or across multiple environments for an organization as a whole. For example, PPEMS 6 may be configured to acquire data and provide aggregated performance metrics and predicted behavior analytics across a worker population (e.g., across workers 10 of either or both of environments 8A, 8B). Furthermore, users 20, 24 may set benchmarks for occurrence of any safety incidences, and PPEMS 6 may track actual performance metrics relative to the benchmarks for individuals or defined worker populations.

As another example, PPEMS 6 may further trigger an alert if certain combinations of conditions are present, e.g., to accelerate examination or service of a safety equipment, such as one of respirators 13. In this manner, PPEMS 6 may identify individual respirators 13 or workers 10 for which the metrics do not meet the benchmarks and prompt the users to intervene and/or perform procedures to improve the metrics relative to the benchmarks, thereby ensuring compliance and actively managing safety for workers 10.

In accordance with techniques of this disclosure, data hub 14A may receive sets of data from each of the different articles of PPE, wherein each set of data is based at least in part on a type of each of the different articles of PPE. Data hub 14A may generate for display a user interface that contemporaneously includes a plurality of graphical elements that are based at least in part on at least two sets of data that correspond to at least two different articles of PPE of the plurality of different articles of PPE. Data hub 14A, in response to receiving an indication of user input that corresponds to at least one of the plurality of graphical elements, may perform at least one operation, as described in this disclosure. In some examples, an indication of user input that corresponds to at least one of the plurality of graphical elements comprises a configuration change to a current operation of the at least one of the plurality of graphical elements. In some examples, the configuration change corresponds to a first article of PPE, wherein the configuration change automatically causes another configuration change to a second article of PPE, the first and second articles of PPE each assigned to the particular user. In some examples, automatically causing another configuration change to a second article of PPE, may mean without requiring user intervention to cause the configuration change to the second article of PPE.

Figure 2:
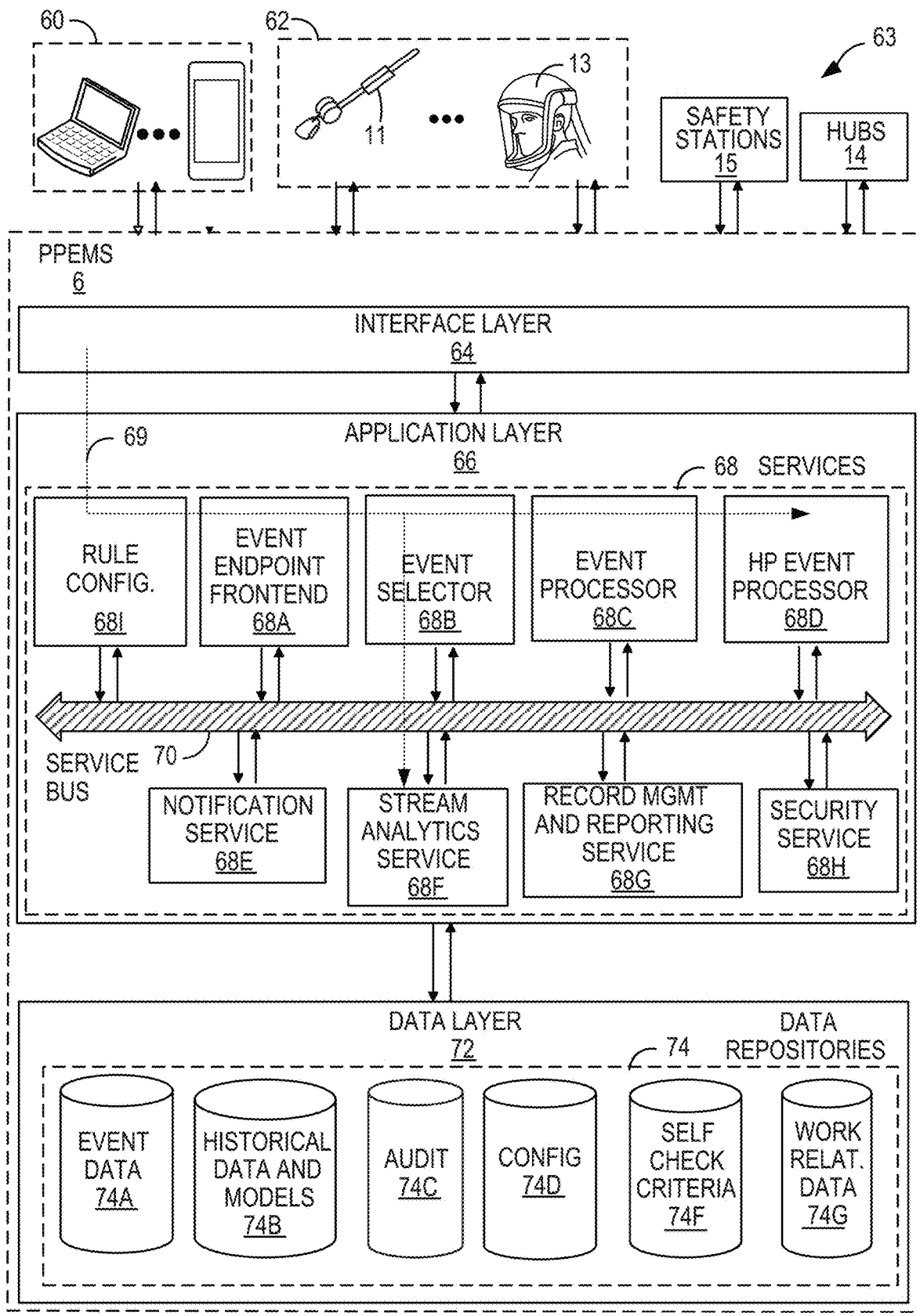
FIG. 2 is a block diagram illustrating an operating perspective of the personal protection equipment management system shown in FIG. 1 in accordance with various techniques of this disclosure.

FIG. 2 is a block diagram providing an operating perspective of PPEMS 6 when hosted as cloud-based platform capable of supporting multiple, distinct work environments 8 having an overall population of workers 10 that have a variety of communication enabled personal protection equipment (PPE), such as safety release lines (SRLs) 11, respirators 13, safety helmets, hearing protection or other safety equipment. In the example of FIG. 2, the components of PPEMS 6 are arranged according to multiple logical layers that implement the techniques of the disclosure. Each layer may be implemented by a one or more modules comprised of hardware, software, or a combination of hardware and software.

In FIG. 2, personal protection equipment (PPEs) 62, such as SRLs 11, respirators 13 and/or other equipment, either directly or by way of hubs 14, as well as computing devices 60, operate as clients 63 that communicate with PPEMS 6 via interface layer 64. Computing devices 60 typically execute client software applications, such as desktop applications, mobile applications, and web applications. Computing devices 60 may represent any of computing devices 16, 18 of FIG. 1. Examples of computing devices 60 may include, but are not limited to a portable or mobile computing device (e.g., smartphone, wearable computing device, tablet), laptop computers, desktop computers, smart television platforms, and servers, to name only a few examples.

As further described in this disclosure, PPEs 62 communicate with PPEMS 6 (directly or via hubs 14) to provide streams of data acquired from embedded sensors and other monitoring circuitry and receive from PPEMS 6 alerts, configuration and other communications. Client applications executing on computing devices 60 may communicate with PPEMS 6 to send and receive information that is retrieved, stored, generated, and/or otherwise processed by services 68. For instance, the client applications may request and edit safety event information including analytical data stored at and/or managed by PPEMS 6. In some examples, client applications may request and display aggregate safety event information that summarizes or otherwise aggregates numerous individual instances of safety events and corresponding data acquired from PPEs 62 and or generated by PPEMS 6. The client applications may interact with PPEMS 6 to query for analytics information about past and predicted safety events, behavior trends of workers 10, to name only a few examples. In some examples, the client applications may output for display information received from PPEMS 6 to visualize such information for users of clients 63. As further illustrated and described in below, PPEMS 6 may provide information to the client applications, which the client applications output for display in user interfaces.

Clients applications executing on computing devices 60 may be implemented for different platforms but include similar or the same functionality. For instance, a client application may be a desktop application compiled to run on a desktop operating system, such as Microsoft Windows, Apple OS X, or Linux, to name only a few examples. As another example, a client application may be a mobile application compiled to run on a mobile operating system, such as Google Android, Apple iOS, Microsoft Windows Mobile, or BlackBerry OS to name only a few examples. As another example, a client application may be a web application such as a web browser that displays web pages received from PPEMS 6. In the example of a web application, PPEMS 6 may receive requests from the web application (e.g., the web browser), process the requests, and send one or more responses back to the web application. In this way, the collection of web pages, the client-side processing web application, and the server-side processing performed by PPEMS 6 collectively provides the functionality to perform techniques of this disclosure. In this way, client applications use various services of PPEMS 6 in accordance with techniques of this disclosure, and the applications may operate within various different computing environment (e.g., embedded circuitry or processor of a PPE, a desktop operating system, mobile operating system, or web browser, to name only a few examples).

As shown in FIG. 2, PPEMS 6 includes an interface layer 64 that represents a set of application programming interfaces (API) or protocol interface presented and supported by PPEMS 6. Interface layer 64 initially receives messages from any of clients 63 for further processing at PPEMS 6. Interface layer 64 may therefore provide one or more interfaces that are available to client applications executing on clients 63. In some examples, the interfaces may be application programming interfaces (APIs) that are accessible over a network. Interface layer 64 may be implemented with one or more web servers. The one or more web servers may receive incoming requests, process and/or forward information from the requests to services 68, and provide one or more responses, based on information received from services 68, to the client application that initially sent the request. In some examples, the one or more web servers that implement interface layer 64 may include a runtime environment to deploy program logic that provides the one or more interfaces. As further described below, each service may provide a group of one or more interfaces that are accessible via interface layer 64.

In some examples, interface layer 64 may provide Representational State Transfer (RESTful) interfaces that use HTTP methods to interact with services and manipulate resources of PPEMS 6. In such examples, services 68 may generate JavaScript Object Notation (JSON) messages that interface layer 64 sends back to the client application that submitted the initial request. In some examples, interface layer 64 provides web services using Simple Object Access Protocol (SOAP) to process requests from client applications. In still other examples, interface layer 64 may use Remote Procedure Calls (RPC) to process requests from clients 63. Upon receiving a request from a client application to use one or more services 68, interface layer 64 sends the information to application layer 66, which includes services 68.

As shown in FIG. 2, PPEMS 6 also includes an application layer 66 that represents a collection of services for implementing much of the underlying operations of PPEMS 6. Application layer 66 receives information included in requests received from client applications and further processes the information according to one or more of services 68 invoked by the requests. Application layer 66 may be implemented as one or more discrete software services executing on one or more application servers, e.g., physical or virtual machines. That is, the application servers provide runtime environments for execution of services 68. In some examples, the functionality interface layer 64 as described above and the functionality of application layer 66 may be implemented at the same server.

Application layer 66 may include one or more separate software services 68, e.g., processes that communicate, e.g., via a logical service bus 70 as one example Service bus 70 generally represents a logical interconnections or set of interfaces that allows different services to send messages to other services, such as by a publish/subscription communication model. For instance, each of services 68 may subscribe to specific types of messages based on criteria set for the respective service. When a service publishes a message of a particular type on service bus 70, other services that subscribe to messages of that type will receive the message. In this way, each of services 68 may communicate information to one another. As another example, services 68 may communicate in point-to-point fashion using sockets or other communication mechanism. Before describing the functionality of each of services 68, the layers are briefly described herein.

Data layer 72 of PPEMS 6 represents a data repository that provides persistence for information in PPEMS 6 using one or more data repositories 74. A data repository, generally, may be any data structure or software that stores and/or manages data. Examples of data repositories include but are not limited to relational databases, multi-dimensional databases, maps, and hash tables, to name only a few examples.

Data layer 72 may be implemented using Relational Database Management System (RDBMS) software to manage information in data repositories 74. The RDBMS software may manage one or more data repositories 74, which may be accessed using Structured Query Language (SQL). Information in the one or more databases may be stored, retrieved, and modified using the RDBMS software. In some examples, data layer 72 may be implemented using an Object Database Management System (ODBMS), Online Analytical Processing (OLAP) database or other suitable data management system.

As shown in FIG. 2, each of services 68A-68I ("services 68") is implemented in a modular form within PPEMS 6. Although shown as separate modules for each service, in some examples the functionality of two or more services may be combined into a single module or component. Each of services 68 may be implemented in software, hardware, or a combination of hardware and software. Moreover, services 68 may be implemented as standalone devices, separate virtual machines or containers, processes, threads or software instructions generally for execution on one or more physical processors.

In some examples, one or more of services 68 may each provide one or more interfaces that are exposed through interface layer 64. Accordingly, client applications of computing devices 60 may call one or more interfaces of one or more of services 68 to perform techniques of this disclosure.

In accordance with techniques of the disclosure, services 68 may include an event processing platform including an event endpoint frontend 68A, event selector 68B, event processor 68C and high priority (HP) event processor 68D. Event endpoint frontend 68A operates as a front end interface for receiving and sending communications to PPEs 62 and hubs 14. In other words, event endpoint frontend 68A operates to as a front line interface to safety equipment deployed within environments 8 and utilized by workers 10. In some instances, event endpoint frontend 68A may be implemented as a plurality of tasks or jobs spawned to receive individual inbound communications of event streams 69 from the PPEs 62 carrying data sensed and captured by the safety equipment. When receiving event streams 69, for example, event endpoint frontend 68A may spawn tasks to quickly enqueue an inbound communication, referred to as an event, and close the communication session, thereby providing high-speed processing and scalability. Each incoming communication may, for example, carry recently captured data representing sensed conditions, motions, temperatures, actions or other data, generally referred to as events. Communications exchanged between the event endpoint frontend 68A and the PPEs may be real-time or pseudo real-time depending on communication delays and continuity.

Event selector 68B operates on the stream of events 69 received from PPEs 62 and/or hubs 14 via frontend 68A and determines, based on rules or classifications, priorities associated with the incoming events. Based on the priorities, event selector 68B enqueues the events for subsequent processing by event processor 68C or high priority (HP) event processor 68D. Additional computational resources and objects may be dedicated to HP event processor 68D so as to ensure responsiveness to critical events, such as incorrect usage of PPEs, use of incorrect filters and/or respirators based on geographic locations and conditions, failure to properly secure SRLs 11 and the like. Responsive to processing high priority events, HP event processor 68D may immediately invoke notification service 68E to generate alerts, instructions, warnings or other similar messages to be output to SRLs 11, respirators 13, hubs 14 and/or remote users 20, 24. Events not classified as high priority are consumed and processed by event processor 68C.

In general, event processor 68C or high priority (HP) event processor 68D operate on the incoming streams of events to update event data 74A within data repositories 74. In general, event data 74A may include all or a subset of usage data obtained from PPEs 62. For example, in some instances, event data 74A may include entire streams of samples of data obtained from electronic sensors of PPEs 62. In other instances, event data 74A may include a subset of such data, e.g., associated with a particular time period or activity of PPEs 62.

Event processors 68C, 68D may create, read, update, and delete event information stored in event data 74A. Event information may be stored in a respective database record as a structure that includes name/value pairs of information, such as data tables specified in row/column format. For instance, a name (e.g., column) may be "worker ID" and a value may be an employee identification number. An event record may include information such as, but not limited to: worker identification, PPE identification, acquisition timestamp(s) and data indicative of one or more sensed parameters.

In addition, event selector 68B directs the incoming stream of events to stream analytics service 68F, which is configured to perform in depth processing of the incoming stream of events to perform real-time analytics. Stream analytics service 68F may, for example, be configured to process and compare multiple streams of event data 74A with historical data and models 74B in real-time as event data 74A is received. In this way, stream analytic service 68F may be configured to detect anomalies, transform incoming event data values, trigger alerts upon detecting safety concerns based on conditions or worker behaviors. Historical data and models 74B may include, for example, specified safety rules, business rules and the like. In addition, stream analytic service 68F may generate output for communicating to PPEs 62 by notification service 68E or computing devices 60 by way of record management and reporting service 68D.

In this way, analytics service 68F processes inbound streams of events, potentially hundreds or thousands of streams of events, from enabled safety PPEs 62 utilized by workers 10 within environments 8 to apply historical data and models 74B to compute assertions, such as identified anomalies or predicted occurrences of imminent safety events based on conditions or behavior patterns of the workers. Analytics service 68F may publish the assertions to notification service 68E and/or record management by service bus 70 for output to any of clients 63.

In this way, analytics service 68F may be configured as an active safety management system that predicts imminent safety concerns and provides real-time alerting and reporting. In addition, analytics service 68F may be a decision support system that provides techniques for processing inbound streams of event data to generate assertions in the form of statistics, conclusions, and/or recommendations on an aggregate or individualized worker and/or PPE basis for enterprises, safety officers and other remote users. For instance, analytics service 68F may apply historical data and models 74B to determine, for a particular worker, the likelihood that a safety event is imminent for the worker based on detected behavior or activity patterns, environmental conditions and geographic locations. In some examples, analytics service 68F may determine whether a worker is currently impaired, e.g., due to exhaustion, sickness or alcohol/drug use, and may require intervention to prevent safety events. As yet another example, analytics service 68F may provide comparative ratings of workers or type of safety equipment in a particular environment 8.

Hence, analytics service 68F may maintain or otherwise use one or more models that provide risk metrics to predict safety events. Analytics service 68F may also generate order sets, recommendations, and quality measures. In some examples, analytics service 68F may generate user interfaces based on processing information stored by PPEMS 6 to provide actionable information to any of clients 63. For example, analytics service 68F may generate dashboards, alert notifications, reports and the like for output at any of clients 63. Such information may provide various insights regarding baseline ("normal") operation across worker populations, identifications of any anomalous workers engaging in abnormal activities that may potentially expose the worker to risks, identifications of any geographic regions within environments for which unusually anomalous (e.g., high) safety events have been or are predicted to occur, identifications of any of environments exhibiting anomalous occurrences of safety events relative to other environments, and the like.

Although other technologies can be used, in one example implementation, analytics service 68F utilizes machine learning when operating on streams of safety events so as to perform real-time analytics. That is, analytics service 68F includes executable code generated by application of machine learning to training data of event streams and known safety events to detect patterns. The executable code may take the form of software instructions or rule sets and is generally referred to as a model that can subsequently be applied to event streams 69 for detecting similar patterns and predicting upcoming events.

Analytics service 68F may, in some example, generate separate models for a particular worker, a particular population of workers, a particular environment, or combinations thereof. Analytics service 68F may update the models based on usage data received from PPEs 62. For example, analytics service 68F may update the models for a particular worker, a particular population of workers, a particular environment, or combinations thereof based on data received from PPEs 62. In some examples, usage data may include incident reports, air monitoring systems, manufacturing production systems, or any other information that may be used to a train a model.

Alternatively, or in addition, analytics service 68F may communicate all or portions of the generated code and/or the machine learning models to hubs 16 (or PPEs 62) for execution thereon so as to provide local alerting in near-real time to PPEs. Example machine learning techniques that may be employed to generate models 74B can include various learning styles, such as supervised learning, unsupervised learning, and semi-supervised learning. Example types of algorithms include Bayesian algorithms, Clustering algorithms, decision-tree algorithms, regularization algorithms, regression algorithms, instance-based algorithms, artificial neural network algorithms, deep learning algorithms, dimensionality reduction algorithms and the like. Various examples of specific algorithms include Bayesian Linear Regression, Boosted Decision Tree Regression, and Neural Network Regression, Back Propagation Neural Networks, the Apriori algorithm, K-Means Clustering, k-Nearest Neighbour (kNN), Learning Vector Quantization (LVQ), Self-Organizing Map (SOM), Locally Weighted Learning (LWL), Ridge Regression, Least Absolute Shrinkage and Selection Operator (LASSO), Elastic Net, and Least-Angle Regression (LARS), Principal Component Analysis (PCA) and Principal Component Regression (PCR).

Record management and reporting service 68G processes and responds to messages and queries received from computing devices 60 via interface layer 64. For example, record management and reporting service 68G may receive requests from client computing devices for event data related to individual workers, populations or sample sets of workers, geographic regions of environments 8 or environments 8 as a whole, individual or groups/types of PPEs 62. In response, record management and reporting service 68G accesses event information based on the request. Upon retrieving the event data, record management and reporting service 68G constructs an output response to the client application that initially requested the information. In some examples, the data may be included in a document, such as an HTML document, or the data may be encoded in a JSON format or presented by a dashboard application executing on the requesting client computing device. For instance, as further described in this disclosure, example user interfaces that include the event information are depicted in the figures.

As additional examples, record management and reporting service 68G may receive requests to find, analyze, and correlate PPE event information. For instance, record management and reporting service 68G may receive a query request from a client application for event data 74A over a historical time frame, such as a user can view PPE event information over a period of time and/or a computing device can analyze the PPE event information over the period of time.

In example implementations, services 68 may also include security service 68H that authenticate and authorize users and requests with PPEMS 6. Specifically, security service 68H may receive authentication requests from client applications and/or other services 68 to access data in data layer 72 and/or perform processing in application layer 66. An authentication request may include credentials, such as a username and password. Security service 68H may query security data 74A to determine whether the username and password combination is valid. Configuration data 74D may include security data in the form of authorization credentials, policies, and any other information for controlling access to PPEMS 6. As described above, security data 74A may include authorization credentials, such as combinations of valid usernames and passwords for authorized users of PPEMS 6. Other credentials may include device identifiers or device profiles that are allowed to access PPEMS 6.

Security service 68H may provide audit and logging functionality for operations performed at PPEMS 6. For instance, security service 68H may log operations performed by services 68 and/or data accessed by services 68 in data layer 72. Security service 68H may store audit information such as logged operations, accessed data, and rule processing results in audit data 74C. In some examples, security service 68H may generate events in response to one or more rules being satisfied. Security service 68H may store data indicating the events in audit data 74C.

In the example of FIG. 2, a safety manager may initially configure one or more safety rules. As such, remote user 24 may provide one or more user inputs at computing device 18 that configure a set of safety rules for work environment 8A and 8B. For instance, a computing device 60 of the safety manager may send a message that defines or specifies the safety rules. Such message may include data to select or create conditions and actions of the safety rules. PPEMS 6 may receive the message at interface layer 64 which forwards the message to rule configuration component 68I. Rule configuration component 68I may be combination of hardware and/or software that provides for rule configuration including, but not limited to: providing a user interface to specify conditions and actions of rules, receive, organize, store, and update rules included in safety rules data store 75E.

Safety rules data store 75E may be a data store that includes data representing one or more safety rules. Safety rules data store 75E may be any suitable data store such as a relational database system, online analytical processing database, object-oriented database, or any other type of data store. When rule configuration component 68I receives data defining safety rules from computing device 60 of the safety manager, rule configuration component 68I may store the safety rules in safety rules data store 75E.

In some examples, storing the safety rules may include associating a safety rule with context data, such that rule configuration component 68I may perform a lookup to select safety rules associated with matching context data. Context data may include any data describing or characterizing the properties or operation of a worker, worker environment, article of PPE, or any other entity. Context data of a worker may include, but is not limited to: a unique identifier of a worker, type of worker, role of worker, physiological or biometric properties of a worker, experience of a worker, training of a worker, time worked by a worker over a particular time interval, location of the worker, or any other data that describes or characterizes a worker. Context data of an article of PPE may include, but is not limited to: a unique identifier of the article of PPE; a type of PPE of the article of PPE; a usage time of the article of PPE over a particular time interval; a lifetime of the PPE; a component included within the article of PPE; a usage history across multiple users of the article of PPE; contaminants, hazards, or other physical conditions detected by the PPE, expiration date of the article of PPE; operating metrics of the article of PPE. Context data for a work environment may include, but is not limited to: a location of a work environment, a boundary or perimeter of a work environment, an area of a work environment, hazards within a work environment, physical conditions of a work environment, permits for a work environment, equipment within a work environment, owner of a work environment, responsible supervisor and/or safety manager for a work environment.

Table 4, shown below, includes a non-limiting set of rules that may be stored to safety rules data store 75E:

TABLE 4

SAFETY RULES

Hub shall immediately assert an "Attention Initial" Alert if Visor Position Status is OPEN in current location requiring Visor Open Allow = NO
Hub shall immediately assert a "Critical Initial" Alert if Filter Type Status is not equal to Filter Type or no filter found required by current location
Hub shall store all alerts in a queue.

TABLE 4-continued

SAFETY RULES

Critical Alerts shall be highest priority in alert queue
Attention Alerts shall have secondary priority in alert queue
Hub shall immediately remove an alert from the queue if its conditions causing the alert have been corrected
A newly added alert to the alert queue shall be flagged as "Active", if it is higher priority than any other alarms in the queue.
A newly added alert to the alert queue shall be flagged as "Active", if all other alarms in the queue are Acknowledged or Notify
A newly added alert to the alert queue shall be flagged as "Pending" if an Active alert already exists in the queue and the newly added alert is lower in priority than the currently Active alert
If an Active alert in the queue is replaced by a new Active alert because of priority, the replaced alert shall be flagged as "Pending"
An active alert shall enable its respective haptic feedback and LED pattern
Hub shall assert an Acknowledge event when user presses and releases button within <3 seconds. (Button_Tap)
Upon an Acknowledge event the Hub shall immediately flag the currently Active alert as Acknowledged, if any Active alerts are in the queue.
An Acknowledged alert shall disable its respective haptic feedback and LED pattern
Upon an Acknowledge event the Hub shall immediately flag the highest priority Pending alert as Active, if any Pending alerts exist in the queue.
Upon an Acknowledge event the Hub shall immediately flag the highest priority Acknowledged alert as Notify, if no Active alerts or Pending exist in the queue.
A Notify alert shall disable its respective haptic feedback and enable its LED pattern
Immediate Cloud Updates - Hub shall send safety violation asserted message via Wi-Fi to cloud service immediately upon assertion of alert
Immediate Worker Interface Updates - Hub shall send safety rule violation alerts asserted message via BLE to Worker Interface immediately upon assertion of alert
Immediate Cloud Updates - Hub shall send safety violation deasserted message via Wi-Fi to cloud service immediately upon deassertion of alert
Immediate Worker Interface Updates - Hub shall send safety violation deasserted message via BLE to Worker Interface immediately upon deassertion of alert It should be understood that the examples of Table 4 are provided for purposes of illustration only, and that other rules may be developed.

Figure 4:
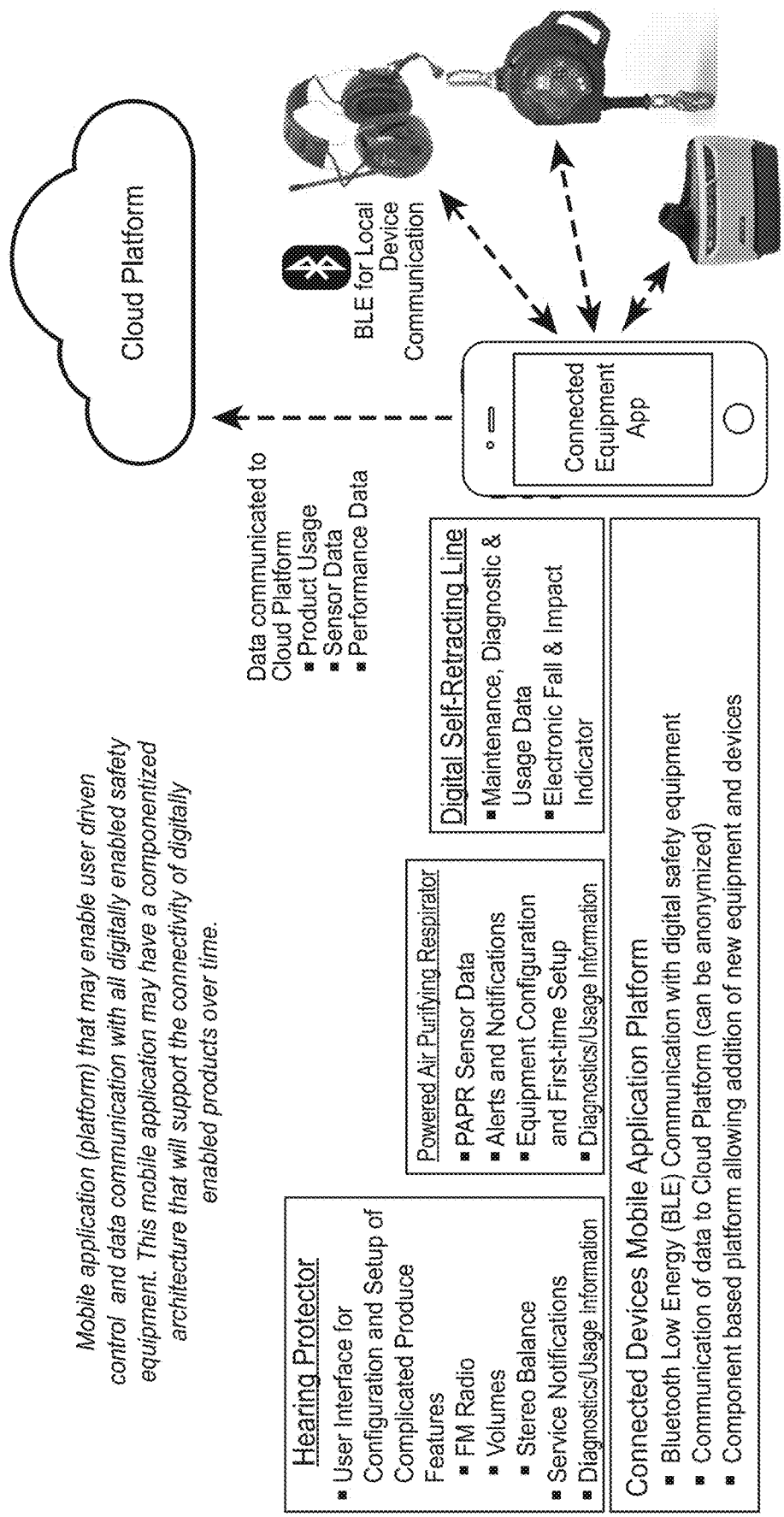
FIG. 4 illustrates an example architecture and descriptive for systems and techniques of this disclosure.

According to aspects of this disclosure, the rules may be used for purposes of reporting, to generate alerts, or the like. In an example for purposes of illustration, worker 10A may be equipped with respirator 13A and data hub 14A. Respirator 13A may include a filter to remove particulates but not organic vapors. Data hub 14A may be initially configured with and store a unique identifier of worker 10A. When initially assigning the respirator 13A and data hub to worker 10A, a computing device operated by worker 10A and/or a safety manager may cause RMRS 68G to store a mapping in work relation data 74G. Work relation data 74G may include mappings between data that corresponds to PPE, workers, and work environments. Work relation data 74G may be any suitable datastore for storing, retrieving, updating and deleting data. RMRS 69G may store a mapping between the unique identifier of worker 10A and a unique device identifier of data hub 14A. Work relation data store 74G may also map a worker to an environment. In the example of FIG. 4, self-check component 68I may receive or otherwise determine data from work relation data 74G for data hub 14A, worker 10A, and/or PPE associated with or assigned to worker 10A.

Worker 10A may initially put on respirator 13A and data hub 14A prior to entering environment 8A. As worker 10A approaches environment 8A and/or has entered environment 8A, data hub 14A may determine that worker 10A is within a threshold distance of entering environment 8A or has entered environment 8A. Data hub 14A may determine that it is within a threshold distance of entering environment 8A or has entered environment 8A and send a message that includes context data to PPEMS 6 that indicates data hub 14A is within a threshold distance of entering environment 8A.

According to aspects of this disclosure, as noted above, PPEMS 6 may additionally or alternatively apply analytics to predict the likelihood of a safety event. As noted above, a safety event may refer to activities of a worker 10 using PPE 62, a condition of PPE 62, or a hazardous environmental condition (e.g., that the likelihood of a safety event is relatively high, that the environment is dangerous, that SRL 11 is malfunctioning, that one or more components of SRL 11 need to be repaired or replaced, or the like). For example, PPEMS 6 may determine the likelihood of a safety event based on application of usage data from PPE 62 to historical data and models 74B. That is, PEMS 6 may apply historical data and models 74B to usage data from respirators 13 in order to compute assertions, such as anomalies or predicted occurrences of imminent safety events based on environmental conditions or behavior patterns of a worker using a respirator 13.

PPEMS 6 may apply analytics to identify relationships or correlations between sensed data from respirators 13, environmental conditions of environment in which respirators 13 are located, a geographic region in which respirators 13 are located, and/or other factors. PPEMS 6 may determine, based on the data acquired across populations of workers 10, which particular activities, possibly within certain environment or geographic region, lead to, or are predicted to lead to, unusually high occurrences of safety events. PPEMS 6 may generate alert data based on the analysis of the usage data and transmit the alert data to PPEs 62 and/or hubs 14. Hence, according to aspects of this disclosure, PPEMS 6 may determine usage data of respirator 13, generate status indications, determine performance analytics, and/or perform prospective/preemptive actions based on a likelihood of a safety event.

For example, according to aspects of this disclosure, usage data from respirators 13 may be used to determine usage statistics. For example, PPEMS 6 may determine, based on usage data from respirators 13, a length of time that one or more components of respirator 13 (e.g., head top, blower, and/or filter) have been in use, an instantaneous velocity or acceleration of worker 10 (e.g., based on an accelerometer included in respirators 13 or hubs 14), a temperature of one or more components of respirator 13 and/or worker 10, a location of worker 10, a number of times or frequency with which a worker 10 has performed a self-check of respirator 13 or other PPE, a number of times or frequency with which a visor of respirator 13 has been opened or closed, a filter/cartridge consumption rate, fan/blower usage (e.g., time in use, speed, or the like), battery usage (e.g., charge cycles), or the like.

According to aspects of this disclosure, PPEMS 6 may use the usage data to characterize activity of worker 10. For example, PPEMS 6 may establish patterns of productive and nonproductive time (e.g., based on operation of respirator 13 and/or movement of worker 10), categorize worker movements, identify key motions, and/or infer occurrence of key events. That is, PPEMS 6 may obtain the usage data, analyze the usage data using services 68 (e.g., by comparing the usage data to data from known activities/events), and generate an output based on the analysis.

In some examples, the usage statistics may be used to determine when respirator 13 is in need of maintenance or replacement. For example, PPEMS 6 may compare the usage data to data indicative of normally operating respirators 13 in order to identify defects or anomalies. In other examples, PPEMS 6 may also compare the usage data to data indicative of a known service life statistics of respirators 13. The usage statistics may also be used to provide an understanding how respirators 13 are used by workers 10 to product developers in order to improve product designs and performance. In still other examples, the usage statistics may be used to gathering human performance metadata to develop product specifications. In still other examples, the usage statistics may be used as a competitive benchmarking tool. For example, usage data may be compared between customers of respirators 13 to evaluate metrics (e.g. productivity, compliance, or the like) between entire populations of workers outfitted with respirators 13.

Additionally or alternatively, according to aspects of this disclosure, usage data from respirators 13 may be used to determine status indications. For example, PPEMS 6 may determine that a visor of a respirator 13 is up in hazardous work area. PPEMS 6 may also determine that a worker 10 is fitted with improper equipment (e.g., an improper filter for a specified area), or that a worker 10 is present in a restricted/closed area. PPEMS 6 may also determine whether worker temperature exceeds a threshold, e.g., in order to prevent heat stress. PPEMS 6 may also determine when a worker 10 has experienced an impact, such as a fall.

Additionally or alternatively, according to aspects of this disclosure, usage data from respirators 13 may be used to assess performance of worker 10 wearing respirator 13. For example, PPEMS 6 may, based on usage data from respirators 13, recognize motion that may indicate a pending fall by worker 10 (e.g., via one or more accelerometers included in respirators 13 and/or hubs 14). In some instances, PPEMS 6 may, based on usage data from respirators 13, infer that a fall has occurred or that worker 10 is incapacitated. PPEMS 6 may also perform fall data analysis after a fall has occurred and/or determine temperature, humidity and other environmental conditions as they relate to the likelihood of safety events.

As another example, PPEMS 6 may, based on usage data from respirators 13, recognize motion that may indicate fatigue or impairment of worker 10. For example, PPEMS 6 may apply usage data from respirators 13 to a safety learning model that characterizes a motion of a user of at least one respirator. In this example, PPEMS 6 may determine that the motion of a worker 10 over a time period is anomalous for the worker 10 or a population of workers 10 using respirators 13.

Additionally or alternatively, according to aspects of this disclosure, usage data from respirators 13 may be used to determine alerts and/or actively control operation of respirators 13. For example, PPEMS 6 may determine that a safety event such as equipment failure, a fall, or the like is imminent. PPEMS 6 may send data to respirators 13 to change an operating condition of respirators 13. In an example for purposes of illustration, PPEMS 6 may apply usage data to a safety learning model that characterizes an expenditure of a filter of one of respirators 13. In this example, PPEMS 6 may determine that the expenditure is higher than an expected expenditure for an environment, e.g., based on conditions sensed in the environment, usage data gathered from other workers 10 in the environment, or the like. PPEMS 6 may generate and transmit an alert to worker 10 that indicates that worker 10 should leave the environment and/or active control of respirator 13. For example, PPEMS 6 may cause respirator to reduce a blower speed of a blower of respirator 13 in order to provide worker 10 with substantial time to exit the environment.

PPEMS 6 may generate, in some examples, a warning when worker 10 is near a hazard in one of environments 8 (e.g., based on location data gathered from a location sensor (GPS or the like) of respirators 13). PPEMS 6 may also apply usage data to a safety learning model that characterizes a temperature of worker 10. In this example, PPEMS 6 may determine that the temperature exceeds a temperature associated with safe activity over the time period and alert worker 10 to the potential for a safety event due to the temperature.

In another example, PPEMS 6 may schedule preventative maintenance or automatically purchase components for respirators 13 based on usage data. For example, PPEMS 6 may determine a number of hours a blower of a respirator 13 has been in operation, and schedule preventative maintenance of the blower based on such data. PPEMS 6 may automatically order a filter for respirator 13 based on historical and/or current usage data from the filter.

Again, PPEMS 6 may determine the above-described performance characteristics and/or generate the alert data based on application of the usage data to one or more safety learning models that characterizes activity of a user of one of respirators 13. The safety learning models may be trained based on historical data or known safety events. However, while the determinations are described with respect to PPEMS 6, as described in greater detail herein, one or more other computing devices, such as hubs 14 or respirators 13 may be configured to perform all or a subset of such functionality.

In some examples, a safety learning model is trained using supervised and/or reinforcement learning techniques. The safety learning model may be implemented using any number of models for supervised and/or reinforcement learning, such as but not limited to, an artificial neural network, a decision tree, naïve Bayes network, support vector machine, or k-nearest neighbor model, to name only a few examples. In some examples, PPEMS 6 initially trains the safety learning model based on a training set of metrics and corresponding to safety events. The training set may include a set of feature vectors, where each feature in the feature vector represents a value for a particular metric. As further example description, PPEMS 6 may select a training set comprising a set of training instances, each training instance comprising an association between usage data and a safety event. The usage data may comprise one or more metrics that characterize at least one of a user, a work environment, or one or more articles of PPE. PPEMS 6 may, for each training instance in the training set, modify, based on particular usage data and a particular safety event of the training instance, the safety learning model to change a likelihood predicted by the safety learning model for the particular safety event in response to subsequent usage data applied to the safety learning model. In some examples, the training instances may be based on real-time or periodic data generated while PPEMS 6 managing data for one or more articles of PPE, workers, and/or work environments. As such, one or more training instances of the set of training instances may be generated from use of one or more articles of PPE after PPEMS 6 performs operations relating to the detection or prediction of a safety event for PPE, workers, and/or work environments that are currently in use, active, or in operation.

Some example metrics may include any characteristics or data described in this disclosure that relate to PPE, a worker, or a work environment, to name only a few examples. For instance, example metrics may include but are not limited to: worker identity, worker motion, worker location, worker age, worker experience, worker physiological parameters (e.g., heart rate, temperature, blood oxygen level, chemical compositions in blood, or any other measureable physiological parameter), or any other data descriptive of a worker or worker behavior. Example metrics may include but are not limited to: PPE type, PPE usage, PPE age, PPE operations, or any other data descriptive of PPE or PPE use. Example metrics may include but are not limited to: work environment type, work environment location, work environment temperature, work environment hazards, work environment size, or any other data descriptive of a work environment.

Each feature vector may also have a corresponding safety event. As described in this disclosure, a safety event may include but is not limited to: activities of a user of personal protective equipment (PPE), a condition of the PPE, or a hazardous environmental condition to name only a few examples. By training a safety learning model based on the training set, a safety learning model may be configured by PPEMS 6 to, when applying a particular feature vector to the safety learning model, generate higher probabilities or scores for safety events that correspond to training feature vectors that are more similar to the particular feature set. In the same way, the safety learning model may be configured by PPEMS 6 to, when applying a particular feature vector to the safety learning model, generate lower probabilities or scores for safety events that correspond to training feature vectors that are less similar to the particular feature set. Accordingly, the safety learning model may be trained, such that upon receiving a feature vector of metrics, the safety learning model may output one or more probabilities or scores that indicate likelihoods of safety events based on the feature vector. As such, PPEMS 6 may select likelihood of the occurrence as a highest likelihood of occurrence of a safety event in the set of likelihoods of safety events.

In some instances, PPEMS 6 may apply analytics for combinations of PPE. For example, PPEMS 6 may draw correlations between users of respirators 13 and/or the other PPE (such as fall protection equipment, head protection equipment, hearing protection equipment, or the like) that is used with respirators 13. That is, in some instances, PPEMS 6 may determine the likelihood of a safety event based not only on usage data from respirators 13, but also from usage data from other PPE being used with respirators 13. In such instances, PPEMS 6 may include one or more safety learning models that are constructed from data of known safety events from one or more devices other than respirators 13 that are in use with respirators 13.

In some examples, a safety learning model is based on safety events from one or more of a worker, article of PPE, and/or work environment having similar characteristics (e.g., of a same type). In some examples the "same type" may refer to identical but separate instances of PPE. In other examples the "same type" may not refer to identical instances of PPE. For instance, although not identical, a same type may refer to PPE in a same class or category of PPE, same model of PPE, or same set of one or more shared functional or physical characteristics, to name only a few examples. Similarly, a same type of work environment or worker may refer to identical but separate instances of work environment types or worker types. In other examples, although not identical, a same type may refer to a worker or work environment in a same class or category of worker or work environment or same set of one or more shared behavioral, physiological, environmental characteristics, to name only a few examples.

In some examples, to apply the usage data to a model, PPEMS 6 may generate a structure, such as a feature vector, in which the usage data is stored. The feature vector may include a set of values that correspond to metrics (e.g., characterizing PPE, worker, work environment, to name a few examples), where the set of values are included in the usage data. The model may receive the feature vector as input, and based on one or more relations defined by the model (e.g., probabilistic, deterministic or other functions within the knowledge of one of ordinary skill in the art) that has been trained, the model may output one or more probabilities or scores that indicate likelihoods of safety events based on the feature vector.

In general, while certain techniques or functions are described herein as being performed by certain components, e.g., PPEMS 6, respirators 13, or hubs 14, it should be understood that the techniques of this disclosure are not limited in this way. That is, certain techniques described herein may be performed by one or more of the components of the described systems. For example, in some instances, respirators 13 may have a relatively limited sensor set and/or processing power. In such instances, one of hubs 14 and/or PPEMS 6 may be responsible for most or all of the processing of usage data, determining the likelihood of a safety event, and the like. In other examples, respirators 13 and/or hubs 14 may have additional sensors, additional processing power, and/or additional memory, allowing for respirators 13 and/or hubs 14 to perform additional techniques. Determinations regarding which components are responsible for performing techniques may be based, for example, on processing costs, financial costs, power consumption, or the like.

Figure 3:
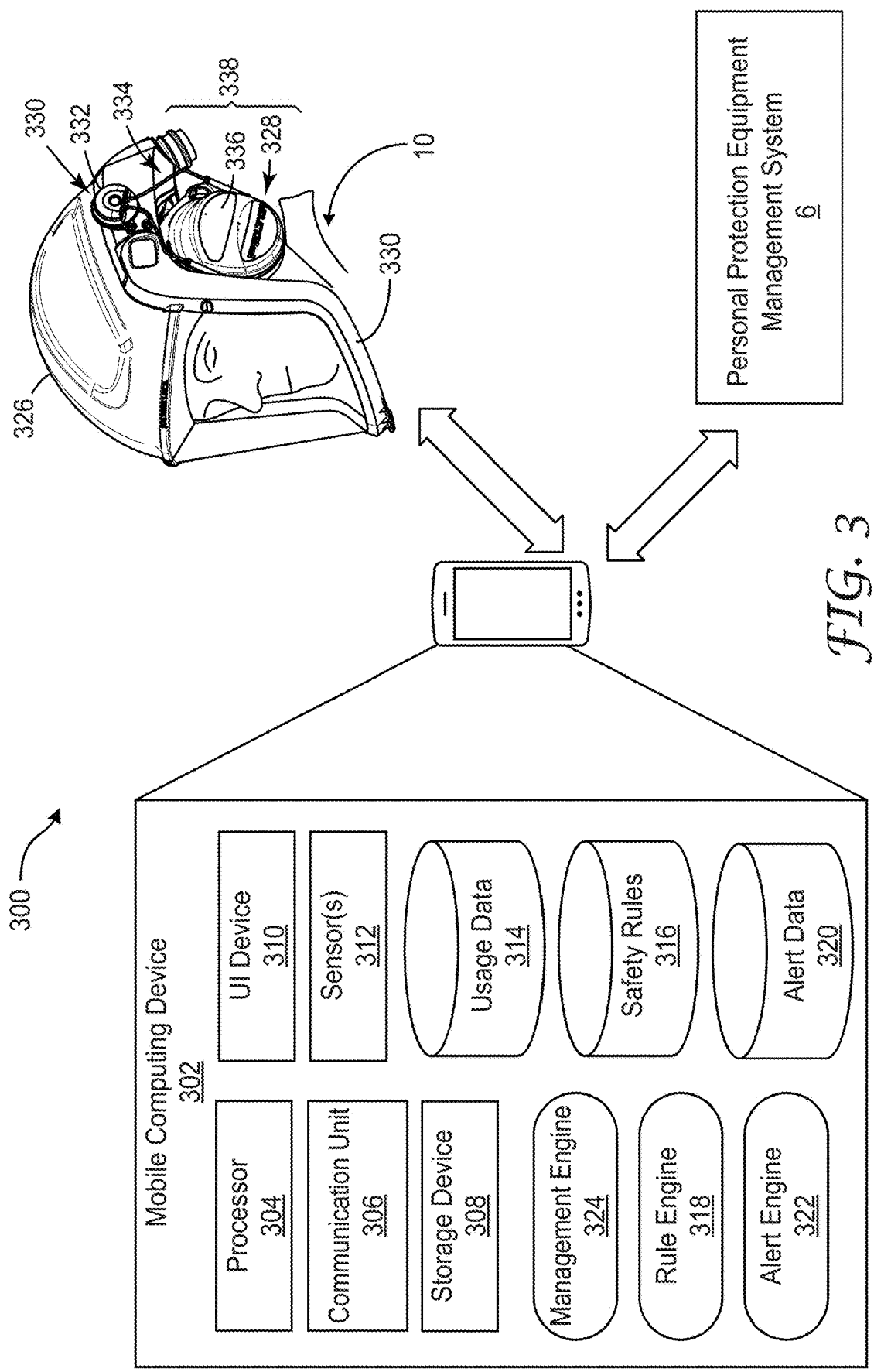
FIG. 3 illustrates an example system including a mobile computing device, a set of personal protection equipment communicatively coupled to the mobile computing device, and a personal protection equipment management system communicatively coupled to the mobile computing device, in accordance with techniques of this disclosure.

FIG. 3 illustrates an example system including a mobile computing device, a set of personal protection equipment communicatively coupled to the mobile computing device, and a personal protection equipment management system communicatively coupled to the mobile computing device, in accordance with techniques of this disclosure. For purposes of illustration only, system 300 includes mobile computing device 302, which may be an example of hub 14A in FIG. 1.

FIG. 3 illustrates components of mobile computing device 302 including processor 304, communication unit 306, storage device 308, user-interface (UI) device 310, sensors 312, usage data 314, safety rules 316, rule engine 318, alert data 320, alert engine 322, and management engine 324. As noted above, mobile computing device 302 represents one example of hubs 14 shown in FIG. 1. Many other examples of mobile computing device 302 may be used in other instances and may include a subset of the components included in example mobile computing device 302 or may include additional components not shown in example mobile computing device 302 in FIG. 3.

In some examples, mobile computing device 302 may be an intrinsically safe computing device, smartphone, wrist- or head-wearable computing device, or any other computing device that may include a set, subset, or superset of functionality or components as shown in mobile computing device 302. Communication channels may interconnect each of the components in mobile computing device 302 for inter-component communications (physically, communicatively, and/or operatively). In some examples, communication channels may include a hardware bus, a network connection, one or more inter-process communication data structures, or any other components for communicating data between hardware and/or software.

Mobile computing device 302 may also include a power source, such as a battery, to provide power to components shown in mobile computing device 302. A rechargeable battery, such as a Lithium Ion battery, can provide a compact and long-life source of power. Mobile computing device 302 may be adapted to have electrical contacts exposed or accessible from the exterior of the hub to allow recharging the mobile computing device 302. As noted above, mobile computing device 302 may be portable such that it can be carried or worn by a user. Mobile computing device 302 can also be personal, such that it is used by an individual and communicates with personal protective equipment (PPE) assigned to that individual. In FIG. 3, mobile computing device 302 may be secured to a user by a strap. However, communication hub may be carried by a user or secured to a user in other ways, such as being secured to PPE being worn by the user, to other garments being worn to a user, being attached to a belt, band, buckle, clip or other attachment mechanism as will be apparent to one of skill in the art upon reading the present disclosure. As described throughout this disclosure, in examples, functionality of mobile computing device 302 may be integrated into one or more articles of PPE, such that a separate mobile computing device 302 is not required to perform the techniques of this disclosure.

One or more processors 304 may implement functionality and/or execute instructions within mobile computing device 302. For example, processor 304 may receive and execute instructions stored by storage device 308. These instructions executed by processor 304 may cause mobile computing device 302 to store and/or modify information, within storage devices 308 during program execution. Processors 304 may execute instructions of components, such as rule engine 318 and alert engine 322 to perform one or more operations in accordance with techniques of this disclosure. That is, rule engine 318 and alert engine 322 may be operable by processor 304 to perform various functions described herein.

One or more communication units 306 of mobile computing device 302 may communicate with external devices by transmitting and/or receiving data. For example, mobile computing device 302 may use communication units 306 to transmit and/or receive radio signals on a radio network such as a cellular radio network. In some examples, communication units 306 may transmit and/or receive satellite signals on a satellite network such as a Global Positioning System (GPS) network. Examples of communication units 306 include a network interface card (e.g. such as an Ethernet card), an optical transceiver, a radio frequency transceiver, a GPS receiver, or any other type of device that can send and/or receive information. Other examples of communication units 306 may include Bluetooth®, GPS, 3G, 4G, and Wi-Fi® radios found in mobile devices as well as Universal Serial Bus (USB) controllers and the like.

One or more storage devices 308 within mobile computing device 302 may store information for processing during operation of mobile computing device 302. In some examples, storage device 308 is a temporary memory, meaning that a primary purpose of storage device 308 is not long-term storage. Storage device 308 may be configured for short-term storage of information as volatile memory and therefore not retain stored contents if deactivated. Examples of volatile memories include random access memories (RAM), dynamic random access memories (DRAM), static random access memories (SRAM), and other forms of volatile memories known in the art.

Storage device 308 may, in some examples, also include one or more computer-readable storage media. Storage device 308 may be configured to store larger amounts of information than volatile memory. Storage device 308 may further be configured for long-term storage of information as non-volatile memory space and retain information after activate/off cycles. Examples of non-volatile memories include magnetic hard discs, optical discs, floppy discs, flash memories, or forms of electrically programmable memories (EPROM) or electrically erasable and programmable (EEPROM) memories. Storage device 308 may store program instructions and/or data associated with components such as rule engine 318 and alert engine 322.

UI device 310 may be configured to receive user input and/or output information to a user. One or more input components of UI device 310 may receive input. Examples of input are tactile, audio, kinetic, and optical input, to name only a few examples. UI device 310 of mobile computing device 302, in one example, include a mouse, keyboard, voice responsive system, video camera, buttons, control pad, microphone or any other type of device for detecting input from a human or machine. In some examples, UI device 310 may be a presence-sensitive input component, which may include a presence-sensitive screen, touch-sensitive screen, etc.

One or more output components of UI device 310 may generate output. Examples of output are data, tactile, audio, and video output. Output components of UI device 310, in some examples, include a presence-sensitive screen, sound card, video graphics adapter card, speaker, cathode ray tube (CRT) monitor, liquid crystal display (LCD), or any other type of device for generating output to a human or machine. Output components may include display components such as cathode ray tube (CRT) monitor, liquid crystal display (LCD), Light-Emitting Diode (LED) or any other type of device for generating tactile, audio, and/or visual output. Output components may be integrated with mobile computing device 302 in some examples.

UI device 310 may include a display, lights, buttons, keys (such as arrow or other indicator keys), and may be able to provide alerts to the user in a variety of ways, such as by sounding an alarm or vibrating. The user interface can be used for a variety of functions. For example, a user may be able to acknowledge or snooze an alert through the user interface. The user interface may also be used to control settings for the head top and/or turbo peripherals that are not immediately within the reach of the user. For example, the turbo may be worn on the lower back where the wearer cannot access the controls without significant difficulty.

Sensors 312 may include one or more sensors that generate data indicative of an activity of a worker 10 associated with mobile computing device 302 and/or data indicative of an environment in which mobile computing device 302 is located. Sensors 312 may include, as examples, one or more accelerometers, one or more sensors to detect conditions present in a particular environment (e.g., sensors for measuring temperature, humidity, particulate content, noise levels, air quality, or any variety of other characteristics of environments in which respirator 13 may be used), or a variety of other sensors.

Mobile computing device 302 may store usage data 314 from components of air respirator system 100. For example, as described herein, components of air respirator system 100 (or any other examples of respirators 13) may generate data regarding operation of system 100 that is indicative of activities of worker 10 and transmit the data in real-time or near real-time to mobile computing device 302.

In some examples, mobile computing device 302 may immediately relay usage data 314 to another computing device, such as PPEMS 6, via communication unit 306. In other examples, storage device 308 may store usage data 314 for some time prior to uploading the data to another device. For example, in some instances, communication unit 306 may be able to communicate with system 100 but may not have network connectivity, e.g., due to an environment in which system 100 is located and/or network outages. In such instances, mobile computing device 302 may store usage data 314 to storage device 308, which may allow the usage data to be uploaded to another device upon a network connection becoming available. Mobile computing device 302 may store safety rules 316 as described in this disclosure. Safety rules 316 may be stored in any suitable data store as described in this disclosure.

System 300 may include head top 326 and hearing protector 328, in accordance with this disclosure. As shown in FIG. 3, head top 326 may include structure and functionality that is similar to or the same as respirator 13A as described in FIG. 1 and other embodiments of this disclosures. Head top 326 (or other headworn device, such as a head band) may include hearing protector 328 that includes, ear muff attachment assembly 330. Ear muff attachment assembly 330 may include housing 332, an arm set 334, and ear muffs 336. Hearing protector 328 may include two separate ear muff cups 336, one of which is visible in FIG. 3 and the other on the opposite side of the user's head and similarly configured to the visible ear muff cup in FIG. 3. Arm set 334 is rotatable between one or more different positions, such that hearing protector 328 may be adjusted and/or toggled, for example, between "active" and "standby" positions (or one or more additional intermediate positions). In an active position, hearing protector 328 is configured to at least partially cover a user's ear. In a standby mode, hearing protector 328 is in a raised position away from and/or out of contact with a user's head. A user is able to switch between active and standby positions when entering or leaving an area necessitating hearing protection, for example, or as may be desired by the user. Adjustment to a standby position allows hearing protector 328 to be readily available for the user to move hearing protector 328 into an active position in which hearing protection is provided without the need to carry or store ear muffs.

Ear muff attachment assembly 330 may be attached directly or indirectly to a helmet, hard hat, strap, head band, or other head support, such as a head top 326. Head top 326 may be worn simultaneously with, and provide a support for, ear muff attachment assembly 330. Ear muff attachment assembly 330 is attached to an outer surface of head top 326, and arm set 334 extends generally downwardly around an edge of head top 326 such that ear muffs of hearing protector 328 may be desirably positioned to cover a user's ear.

In various examples, head top 326 and ear muff attachment assembly 330 may be joined using various suitable attachment components, such as snap-fit components, rivets, mechanical fasteners, adhesive, or other suitable attachment components as known in the art. Ear muffs of hearing protector 328 are configured to cover at least a portion of a user's ear and/or head. In FIG. 3, ear muffs exhibit a cup shape and include a cushion and a sound absorber (not shown). Cushions are configured to contact a user's head and/or ear when ear muffs are in an active position forming an appropriate seal to prevent sound waves from entering. Arm set 334 extends outwardly from head top 326 and is configured to carry ear muffs of hearing protector 328.

In the example of FIG. 3, ear muff attachment assembly 330 may have positional or motion sensors to detect whether the ear muffs are in the standby or active position. The positional or motion sensor may generate one or more signals that indicate a particular position from a set of one or more positions. The signals may indicate one or more position values (e.g., discrete "active"/"standby" values, numeric position representations, or any other suitable encoding or measurement values). If, for example, the standby condition is detected by the one or more positional or motion sensors and if an environmental sound detector detects unsafe sound levels, then a computing device may generate an indication of output, such as a notification, log entry, or other type of output. In some examples, the indication of output may be audible, visual, haptic, or any other physical sensory output.

In high noise environment workers may be required to use hearing protection in the form of ear plugs or ear muffs. Ear muffs typically comprise cup shaped shell with a sound absorbing liner that seals against the ear of the user. Many workers also use head and/or face protection while wearing ear muffs. Therefore, many ear muff models are designed to attach to a helmet, hard hat or other headgear, such as shown in FIG. 3. The ear muffs may be affixed to the headgear via an arm that attaches to the headgear and is adjustable between various positions over or away from the worker's ear.

As described above, headgear mounted ear muffs rotate between two positions: the active position where the ear muffs cover the worker's ears providing hearing protection, and the standby position where the ear muffs are rotated up and away from the ears. While in the standby position the ear muff does not provide hearing protection to the worker. In some types of headgear attached ear muffs, the muffs can be pivoted outward away from the ear of the user in the standby position. In this case, the ear muffs rest at a small distance away from the head of the user. In the active position, the muffs are pivoted toward the head where it is sealed around the ears of the user providing hearing protection.

Returning to mobile computing device 302, safety rules 316 may include threshold information both for a length of time visor is allowed to be in an open position before an alert is generated, and the level or type of contaminants that will trigger an alert. For example, when mobile computing device 302 receives information from an environmental beacon that there are no hazards present in the environment, the threshold for the visor being in the open position may be infinite. If a hazard is present in the environment, then the threshold may be determined based upon the concern of the threat to the user. Radiation, dangerous gases, or toxic fumes would all require assignment of the threshold to be on the order of one second or less.

Thresholds for head top temperature can be used to predict, e.g., by PPEMS 6, heat related illness and more frequent hydration and/or rest periods can be recommended to the user. Thresholds can be used for predicted battery run time. As the battery nears selectable remaining run time, the user can be notified/warned to complete their current task and seek a fresh battery. When a threshold is exceeded for a specific environmental hazard, an urgent alert can be given to the user to evacuate the immediate area. Thresholds can be customized to various levels of openness for the visor. In other words, a threshold for the amount of a time the visor may be open without triggering an alarm may be longer if the visor is in the partially open position as compared to the open position.

Reaching different thresholds set forth in safety rules 316 may result in triggering different types of alerts or alarms. For example, alarms may be informational (not requiring a user response), urgent (repeated and requiring a response or acknowledgement from a user), or emergency (requiring immediate action from a user.) The type of alert or alarm can be tailored to the environment. Different types of alerts and alarms can be coupled together to get user attention. In some instances, a user may be able to "snooze" an alert or alarm.

Rule engine 318 may be a combination of hardware and software that executes one or more safety rules, such as safety rules 316. For instance, rule engine 318 may determine which safety rules to execute based on context data, information included in the safety rule set, other information received from PPEMS 6 or other computing devices, user input from the worker, or any other source of data that indicates which safety rules to execute. In some examples, safety rules 316 may be installed prior to a worker entering a work environment, while in other examples, safety rules 316 be dynamically retrieved by mobile computing device 302 based on context data generated at first particular point in time.

Rule engine 318 may execute safety rules periodically, continuously, or asynchronously. For instance, rule engine 318 may execute safety rules periodically by evaluating the conditions of such rules each time a particular time interval passes or expires (e.g., every second, every minute, etc.). In some examples, rule engine 318 may execute safety rules continuously by checking such conditions using one or more scheduling techniques that continuously evaluate the conditions of such rules. In some examples, rule engine 318 may execute safety rules asynchronously, such as in response to detecting an event. An event may be any detectable occurrence, such as moving to a new location, detecting a worker, coming within a threshold distance of another object, or any other detectable occurrence.

Rule engine 318, upon determining that a condition of a safety rule has or has not been satisfied may perform one or more actions associated with the safety rule by executing one or more operations that define the actions. For instance, rule engine 318 may execute a condition that determines if a worker is approaching or has entered a work environment, (a) whether a PAPR is being worn by the worker and (b) whether the filter in the PAPR of a particular type of filter, e.g., a filter that removes contaminants of a particular type. This safety rule may specify actions if the condition is not satisfied which cause rule engine 318 to generate an alert at mobile computing device 302 using UI device 310 and send a message using communication unit 306 to PPEMS 6, which may cause PPEMS 6 to send a notification to a remote user (e.g., the safety manager).

Alert data 320 may be used for generating alerts for output by UI device 310. For example, mobile computing device 302 may receive alert data from PPEMS 6, end-user computing devices 16, remote users using computing devices 18, safety stations 15, or other computing devices as illustrated in FIG. 1. In some examples, alert data 320 may be based on operation of system 300. For example, mobile computing device 302 may receive alert data 320 that indicates a status of system 300, that system 300 is appropriate for the environment in which system 300 is located, that the environment in which system 300 is located is unsafe, or the like.

In some examples, additionally or alternatively, mobile computing device 302 may receive alert data 320 associated with a likelihood of a safety event. For example, as noted above, PPEMS 6 may, in some examples, apply historical data and models to usage data from system 300 in order to compute assertions, such as anomalies or predicted occurrences of imminent safety events based on environmental conditions or behavior patterns of a worker using system 300. That is, PPEMS 6 may apply analytics to identify relationships or correlations between sensed data from system 300, environmental conditions of environment in which system 300 is located, a geographic region in which system 300 is located, and/or other factors. PPEMS 6 may determine, based on the data acquired across populations of workers 10, which particular activities, possibly within certain environment or geographic region, lead to, or are predicted to lead to, unusually high occurrences of safety events. Mobile computing device 302 may receive alert data 320 from PPEMS 6 that indicates a relatively high likelihood of a safety event.

Alert engine 322 may be a combination of hardware and software that interprets alert data 320 and generate an output at UI device 310 (e.g., an audible, visual, or tactile output) to notify worker 10 of the alert condition (e.g., that the likelihood of a safety event is relatively high, that the environment is dangerous, that system 300 is malfunctioning, that one or more components of system 300 need to be repaired or replaced, or the like). In some instances, alert engine 322 may also interpret alert data 320 and issue one or more commands to system 300 to modify operation or enforce rules of system 300 in order to bring operation of system 300 into compliance with desired/less risky behavior. For example, alert engine 322 may issue commands that control the operation of head top 326 or a clean air supply source.

Various techniques described in this disclosure may be implemented by mobile computing device 320. Although various examples, including the following examples, may be described with respect to an auto-darkening filter of a welding helmet and/or welding equipment, such techniques may be applied to any article of PPE. In some examples, management engine 324 may execute one or more anti-theft techniques in conjunction with articles of PPE, such as a respirator, welding mask, hearing protector, digital SRL or any other type of PPE. In particular, the article of PPE and mobile computing device 320 are linked together by an authentication credential and/or challenge process by which the article of PPE may not operate or be locked to prevent unauthorized use. For instance, if a welding helmet includes an auto-darkening filter, then the filter may remain permanently on to protect the worker's eyes, but without a passcode, or the proximity threshold between PPE and mobile device being satisfied, or other authentication challenge or technique being satisfied, the auto-darkening filter may not turn off to provide the visibility convenience to the user when a welding arc is not present. Management engine 324 may enforce the change in functionality to the article of PPE based on whether the authentication or proximity requirement is satisfied, by sending an indication to the PPE that changes its operation when the requirement is satisfied.

Such anti-theft techniques may, for example, disable light sensors on the welding mask, such that the user takes the welding helmet a distance away from the mobile computing device and/or work environment, the auto-darkening filter is locked in dark mode. Management engine 324 may only permit the welding mask to exit the dark-mode if an authentication challenge and/or proximity require is satisfied, in which case management engine 324 sends an authentication credential or other indication of data to the welding helmet that enables the auto-darkening filter to operate normally (e.g., between dark and light mode based on presence of welding arc). In some examples, the authentication challenge could be implemented with a public key encryption infrastructure in the management engine 324 and a computing device in the article of PPE (e.g., welding helmet). In other examples, a cryptochip may be included in the article of PPE. In response to a particular article of PPE failing the authentication challenge, operation of at least one functionality of the particular article of PPE may be prevented by at least one of the article of PPE and/or a computing device communicatively coupled to the article of PPE.

In some examples, if management engine 324 can communicate with the article of PPE using a short-range wireless communication (e.g., Bluetooth or same WiFi SSID), management engine 324 can assume that the article of PPE and mobile computing device have similar GPS and therefore no theft of the article of PPE has occurred. For instance, management engine 324 may determine that a particular article of PPE is within wireless communication range of the computing device. Management engine 324 may determine, based at least in part on a GPS location of the computing device, that the computing device is within a predefined region. The pre-defined region may correspond to a user-defined or machine-defined region of permitted use for PPE (e.g., a work environment, PPE locker or other pre-defined region). Management engine 324 may determine, based at least in part the determination that the particular article of PPE is within wireless communication range of the computing device and the determination that the computing device is within a predefined region, that the particular article of PPE is authorized for use. For instance, by determining that the computing device is within the pre-defined region and that the article of PPE is within wireless range of the computing device, the computing device may determine that the PPE is authorized for use (e.g., not stolen or otherwise unauthorized). In some examples, management engine 324 may enable, based at least in part on the determination that the particular article of PPE is authorized for use, operation of at least one functionality of the particular article of PPE. For instance, such functionality may include, but is not limited to, enabling an ADF of a welding helmet, enabling retraction of a self-retracting line, enabling a blower fan of a respirator, or any other functionality of any article of PPE. In some examples, a helmet or other PPE may be stolen at a work site but as the auto-darkening filter is "locked" in dark mode, and the ADF needs a password before the ADF can be used as intended.

In some examples, a particular article of PPE determines whether it is within at least one of a threshold distance of the computing device or within wireless communication range of the computing device. In response to determining that the particular article of PPE is not within at least one of a threshold distance of the computing device or within wireless communication range of the computing device, the article of PPE may prevent operation of at least one functionality of the particular article of PPE. In some examples, a computing device communicatively coupled to the article of PPE, rather than the article of PPE itself, may perform one or more of the aforementioned functions.

In some examples, management engine 324 may store and/or use a user identifier to unique identify a specific article of PPE for a user. For instance, mobile computing device 302, may detect multiple respirators in proximity to the mobile computing device. Management engine 324 may be configured with a unique identifier of the article of PPE (e.g., respirator) such that management engine 324 automatically connects to configures communication for the specific article of PPE configured with management engine 324, thereby avoiding inadvertent communication with other articles of PPE not assigned to the user of mobile computing device 302. If an equipment locker has ten different helmets, management engine 324 may pre-configure a personalized helmet for a user of mobile computing device 302 to automatically connect to personalized helmet. For instance, management engine 324 may store a user identifier of a particular user in association with a PPE identifier of a particular article of PPE Management engine 324 may, in response to detecting multiple different PPE within wireless range of the computing device, determine, based at least in part on the user identifier and the PPE identifier, that the computing device is assigned to the particular user and that the particular article of PPE is assigned to the particular user. Management engine 324 may establish a connection, based on the determination that the computing device is assigned to the particular user and that the particular article of PPE is assigned to the particular user, between the computing device and the particular article of PPE. In this way, if multiple PPE are detected (e.g., PPE of the same type), management engine 324 may establish a wireless connection for communication between the computing device assigned to the worker and the particular article of PPE that is assigned to the worker.

In some examples, management engine 324 may be used to locate an article of PPE that is misplaced or otherwise located away from a worker. For instance, management engine 324 may provide a location on a map user interface of where the article of PPE (e.g., a welding mask) is presently located based on location information detected or provided by the article of PPE. For example, management engine 324 may output for display, in a visual map, a graphical indication of a location of a particular article of PPE in the at least two different articles of PPE. In some examples, management engine 324 may determine through a day, locations where the welder is spending her time either welding or not welding. In some instances, management engine 324 may determine a set of locations where the user has used the particular article of PPE; and output for display in the visual map, graphical indications of the respective set of locations where the user has used the particular article of PPE. Management engine 324 may determine locations where the welder was welding and advise a worker to re-investigate those locations to locate the welding mask. In some examples, management engine 324 may determine whether the welding arc is enabled and output for display or otherwise provide those locations in a user interface. As such, the user may retrace her location to identify the article of PPE. In some examples, one or more of the graphical indications in the visual map of the respective set of locations where the user has used the particular article of PPE further indicate that the particular article of PPE was in use at the respective set of locations.

In some examples, management engine 324 may cause the alert engine to output alerts to the auto-darkening filter or other face-positioned surface of an article of PPE. The alert may notify the user of an urgent matter. LED's or the actual ADF could be blinking. As an example, if info about e.g. a gas leak (or her/his children trying to reach her/him on the phone) is communicated to the mobile computing device, management engine 324 may cause the alert engine to notify the user as the ADF starts blinking The user/welder then can remove his protective equipment and to find a solution. As welders often are wearing a lot of protective equipment this could delay the perception of an urgent message, the critical seconds that may make the difference. By alerting the user via the ADF he/she can get needed information faster. The ADF could also be equipped with various sensors and work as a detection device itself. In some examples, the alerting process could affect the function the PPE. For instance, the alert may start as LED on bottom of welding mask and as priority/urgency of message increases, then management engine 324 could turn off ADF on a welding mask. A priority spectrum could be established by management engine 324, based on the article of PPE, age of message or any other contextual information. As the priority increases the alert to the article of PPE may increase, such as disabling a welding arc, permanently enabling dark mode on the welding mask and the like. Accordingly, management engine 324 may generate a message in response to a safety event; determine a priority of the message; and send, based at least in part on the priority of the message, the message to a particular article of PPE in the at least two different articles of PPE.

In some examples, management engine 324 may initiate or execute a self-diagnostic check on an article of PPE such as a welding helmet with an auto-darkening filter. If one or more parameters indicate that the article of PPE is not operating correctly, management engine 324 may perform one or more operations, such as outputting information for display, alerting the user, and/or communicating with PPEMS 6. In some examples, the ADF may run a self check at every start. The users may receive confirmation via management engine 324 which may output information for display. This may provide the user a quick confirmation that the equipment will keep him safe safe or if there is a replacement part that should be changed.

In some examples, management engine 324 may generate, store, send, and/or use statistics about articles of PPE communicatively coupled to mobile computing device 302. For instance, management engine 324 may use such statistics to estimate if battery needs to be replaced. In some examples, management engine 324 may determine that a user has have N number of days of welding based on estimate battery life. Other statistics such as number of arcs initiated, length of arc time, number of ADF mode changes, or any other information about articles of PPE may be determined from the statistics. In some examples, based on historically recorded usage data, management engine 324 may indicate remaining battery capacity to the user. Battery running time may be presented in a user interface generated by management engine 324. In some examples, management engine 324 may receive statistical data about a particular article of PPE in the at least two different articles of PPE; and output for display the statistical data about the particular article of PPE. In some examples, management engine 324 may determine at least one of productivity data or a safety data that corresponds to usage of the particular article of PPE by the user. Management engine 324 may output for display the at least one of productivity data or safety data that is based on the statistical data.

In some examples, management engine 324 may maintain a maintenance schedule for articles of PPE associated with mobile computing device 302. For instance, the maintenance schedule may support the user and keep a log of when spare parts was last changed. A user interface, automated scheduler, or other logic may assist the user to keep track and remind her of service and maintenance intervals. As an example, the welding arc may be measured by the sensor (arc, and heat), then and management engine 324 may measure how much exposure welding shield has and when to replace to ADF.

In some examples, management engine 324 may receive a set of data or "data dump" from one or more articles of PPE. For instance, an ADF "dumps" recorded data to mobile computing device 302. Management engine 324 may present the data/statistics in a comprehensive and/or integrated way in a user interface. Statistics might also be pushed forward to e.g. technical service or to a factory supervisor. E.g. data of "hours in use"/"time in dark state" and other sensors could be used to indicate productivity or safety level. In some examples, such data or the aforementioned statistics may be used for productivity measurements and/or analysis. For instance, management engine 324 may measure hours per shift of arc being in action, compare what is needed for an arc versus what is actually used to weld, identify target arc times that are compared with actual arc time (e.g., using camera vision or motion during art to identify number of seams or time of seams), or perform any other measurement of productivity related to the article of PPE's operation or use. In some examples, management engine 324 may receive user input that indicates the job info for the target arc time, welding site information, welding speeds for certain types of welds, or any other information, which may be synchronized, pre-populated, or otherwise distributed on mobile computing device 302, articles of PPE, and/or PPEMS 6. In some examples, management engine 324 may measure how often the ADF has been used to judge % usage time, meters/time welded/shift/part. In some examples management engine may output for display information in a GUI that indicates measured productivity and/or quality. In some examples, the "productivity data" collected from PPE are presented in a macro view or homepage.

In some examples, different PPE statuses may be output for display by management engine 324 in graphical user interfaces. For instance, a PAPR-status, ADF status, or any other status may be output for display using one or more visual characteristics, such as color, size, shape, image content, animation content and any other visual characteristic. In some examples, mobile computing device 302 may be a wearable computing device (e.g., smartwatch, smart headband, etc) that is wearable on the exterior of a workers PPE garments. In some examples, this wearable computing device may receive gesture inputs that can control the operation of PPE by management engine 324 detecting a gesture and sending messages or data that control the operation of different articles of PPE. In some examples, a single gesture may change the operation of multiple different articles of PPE. For example, a "quiet" gesture may turn off a blower on a PAPR, turn off noise cancellation on a headset, and turn the volume off a headset. More generally, a single gesture may be mapped to multiple different operations for multiple different articles of PPE, such that the execution of the single gesture causes the multiple different options to be performed. In some examples, management engine 324 may receive an indication of a gesture performed by the user. Management engine 324 may generate, based at least in part on the gesture, a set of messages that change configurations of each of the at least two different articles of PPE of the plurality of different articles of PPE. Management engine 324 may send the respective messages to the at least two different articles of PPE. Upon receiving the respective messages, each respective article of PPE may change its configuration based on the content of the respective message it receives.

In some examples, mobile computing device 302 may provide for a connected system where a PAPR and a welding head-top can communicate. Management engine and/or the PPE may cause, for example, output at an ADF when PAPR requires a filter replacement. In some examples, other sensors (smoke, gas, pressure, moisture . . . ) may be able to detect hazards/environment, which may if, for example, a respiratory hazard is detected, cause an ADF to display an alert. In this way, management engine 324 may enable an event at one article of PPE to influence the operation or configuration of another article of PPE.

In some examples, management engine 324 may enable the registration of an identifier or serial number of an article of PPE with a manufacturer. In some examples, management engine 324 may identify which product/version that is connected and output for display the relevant spare parts. In some examples, management engine 324 may indicate which suppliers in a geographical region carry these spare parts. In some examples, management engine 324 may generate push-notifications about relevant upgrades/replacements and/or enable the placement of orders of such upgrades/replacements.

In some examples, management engine 324 may store, manage and output for display user instructions, training videos, and the like that are based at least in part on articles of PPE configured with management engine 324. As an example, a worker may query "how to disassemble the head band?", management engine 324 may provide information such as service information with a picture or diagram of a welding helmet and the ADF. The user may provide input such as tapping on the head top, the user interface zooms in, then provides user input to tap on the headband, which causes drawings, instructions and/or videos or other media to be presented to the user. In some examples, management engine 324 may receive an audio signal in response to sound generated by the particular user. Management engine 324 may determine that the audio signal comprises a voice command to select training media associated with a particular article of PPE in the at least two different articles of PPE. Management engine 324 may, in response to selecting the training media associated with a particular article of PPE in the at least two different articles of PPE, output the training media. Management engine 324 may receive a user input that indicates a selection of at least a portion of the training media that corresponds to a specific portion of the particular article of PPE. Management engine 324 may output, in response to the user input, the portion of the training media that corresponds to the specific portion of the particular article of PPE.

In some examples, management engine 324 may manage welding modes and pre-settings. For instance, via management engine 324, different settings of an ADF or other PPE may be changed based on user input including but not limited to voice control or quick buttons provided in different user interfaces generated by management engine 324. As an example, certain settings may be preferable if the user is a TIG welder and others if a different user is a MAG-welder or welding with stick. Recommended settings for different welding situations may be pre-configured in the management engine 324. Management engine 324 may enable a user to save personalized settings e.g. "welding of part #332". Management engine 324 may enable settings that are otherwise not possible using the ADF-located dashboard and could be made available in user interfaces provided by management engine 324 (e.g., stepless adjustments, special welding modes . . . ) since the ADF dashboard on the ADF itself may be limited or restricted to a finite number of LED's and buttons.

In the example of voice control, management engine 324 may receive an audio signal in response to sound generated by the particular user. Management engine 324 may determine that the audio signal comprises a voice command to change a configuration associated with a particular article of PPE of the at least two different articles of PPE based at least in part on the information in the audio signal the corresponds to a particular type of the particular article of PPE. In some examples, management engine 324 may perform natural language processing on the audio signal to determine the voice command Once the voice command is recognized, management engine 324 may determine one or more configuration changes to be applied to the article of PPE. Management engine 324 may, in response to the determination that the audio signal comprises the voice command to change the configuration associated with the particular article of PPE, generate a message comprising data to change the configuration associated with the particular article of PPE. The data may comprise configuration parameters and/or values and/or settings that correspond to the type of PPE and, when processed by the PPE, change the configuration or operation of the article of PPE. Management engine 324 may send the message to the particular article of PPE. The article of PPE may process the data in the message to change the configuration or operation of the article of PPE.

In some examples, management engine 324 may store a worker's "favorite" settings within a "welding community" by forwarding the user's settings to another user management engine 324. For instance, management engine 324 may determine a set of settings configured by a first user for a particular type of a first article of PPE. In some examples, management engine 324 may select, based on the type of the particular article of PPE, a particular set of settings for the article of PPE that are different than another set of settings for a different type of PPE. Management engine 324 may determine that a second article of PPE controlled by a second user is of the particular type. Management engine 324 may send the set of settings configured by the first user to a computing device controlled by the second user.

In some examples, management engine 324 may provide access and connectivity to a customer service line via VOIP, cellular, or any other type of communication. In this way, the user and customer service representative may resolve any issue the user may be having efficiently. Quick/extended trouble shooting as data and status of the ADF, for example, may be forwarded to customer service and/or the manufacturer of the PPE. As an example, pictures of the PPE or otherwise can be transferred between manufacturer/customer service and the user for help solving problems.

In some examples, management engine 324 may provide remote control, status and usage statistics. For instance, management engine 324 may access app settings and history of PPE. In some examples, settings made via the ADF or other PPE are reflected on mobile computing device 302 and/or the articles of PPE. Management engine 324 may enable more settings via the volume buttons on the phone, voice control via the phone, adjust shade level whilst welding, whereas such functionality may not have been possible without a more expandable user interface. Status of battery and specific errors/warnings may be provided in one or more user interfaces.

In some examples, as described herein, management engine 324 may collect usage statistics and perform operations or processing based on the statistics. For instance, management engine 324 may collect sensor data from e.g. accelerometer sensor and send to manufacturer or customer service to provide info how and where the product has been used. For example, an accelerometer data event may indicate proof of mechanical shock. In some examples, a user may be required to opt in before such hidden data is sent to manufacturer and/or customer service.

In some examples, management engine 324 may impose access controls such as denying or granting access at a safety checkpoint based on connected PPE and/or operating state of the PPE. In some examples, because various functionality may be included in the user interface provided by mobile computing device 302, a user interface of PAPR visor or ADF dashboard may include fewer functions or information that are easier to see and or operate. In some examples, firmware updates may downloaded, scheduled, and/or provided to the ADF or other PPE by management engine 324. In some examples, management engine 324 may communicate with welding equipment (e.g., TIG welder, MIG welder or any other welding device). Communication may occur via Bluetooth or any suitable communication channel and be used to configure communication with a welding machine to achieve secure triggering or control of autoshade. In some examples, management engine 324 may provide for streaming (e.g., audio or video) content to an article of PPE, such as an ADF or visor of a PAPR. In some examples, management engine 324 may enable communication between multiple workers via voice, image, video, and/or textual communication. Via management engine 324, a worker may connect with welding partner and via the app/phone allow communication whilst working. Two workers working together in a noisy environment may be connected in a seamless manner.

In some examples, management engine 324 may detect a change in a setting, configuration or operation of one article of PPE and, in response to the change, automatically change a setting, configuration or operation. For example, if a change in blower speed of a PAPR is detected, management engine 324 may change a noise-cancellation and/or volume level in a hearing protector that is assigned to the worker having the PAPR. Such changes and/or statuses in settings, configurations, or operations that change the settings, configurations, or operations in other articles of PPE may be configured by pre-set rules and/or rules that are learned over time using learning techniques described in this disclosure. In some examples, an indication of user input that corresponds to at least one of the plurality of graphical elements comprises a configuration change to a current operation of the at least one of the plurality of graphical elements. In some examples, the configuration change corresponds to a first article of PPE, wherein the configuration change automatically causes another configuration change to a second article of PPE, the first and second articles of PPE each assigned to the particular user.

In some examples, different articles of PPE may refer to different sub-components of an article of PPE. For instance an article of PPE may be a filter, blower unit, head top, or visor of a PAPR. An article of PPE may be the PAPR with all the sub-component articles of PPE.

FIG. 4 illustrates an example architecture and descriptive for systems and techniques of this disclosure. Techniques of this disclosure relate to a remote interface to digitally enabled safety equipment. A remote interface for safety equipment may enable a new mode of user interaction with the safety equipment and may add new functionality or improve usability of complex or challenging tasks. One such task is changing multiple or complex configuration settings within the safety equipment. Other functionality enabled by a remote interface includes retrieving and viewing equipment data and receiving notifications and alerts on equipment performance. Additionally, usage and performance data can be collected communicated back to the equipment manufacturer for warranty, support and future product development purposes.

In the proposed invention, three components may exist including but not limited to: a Remote Interface, Digitally Enabled Safety Equipment, and a Digital Communication Interface. In the case of the Remote Interface, the proposed remote interface may exist within a software mobile application. This mobile application may have a modular architecture that allows adding new equipment types (Communication headset, Digital SRL, PAPR, etc. . . . ) quickly and efficiently while sharing core application functionality. In the case of Digitally Enabled Safety Equipment, smart, digital safety equipment may have wireless communication and event processing logic to accept and process commands and data requests from the Remote Interface. In the case of the Digital Communication Interface, a local, short range wireless communication protocol may enable communication of data between the Remote Interface and the Safety Equipment. Examples of such an interface include Bluetooth Low Energy (BLE) and Near Field Communication (NFC).

In some examples, techniques of this disclosure may provide for Modification of Safety Equipment Configuration. For instance, conventional safety equipment (or personal protection equipment) may have a limited capability or functionality to provide a convenient and easy to use user interface. Due to restrictions related to durability and cost, a small number of buttons and indicators may often be all that is available for users to change configuration and settings of their conventional safety equipment. Leveraging a remote interface within a smartphone application opens up additional options available within a Graphical User Interface. One example of this functionality is proposed for changing the radio station within a hearing protector such as a Peltor WS ALERT XPI communication headset. The hardware interface on the XPI headset may contain a single up and down button for changing the radio station, the user guide instructions are shown in FIG. 5A.

Figure 5A:
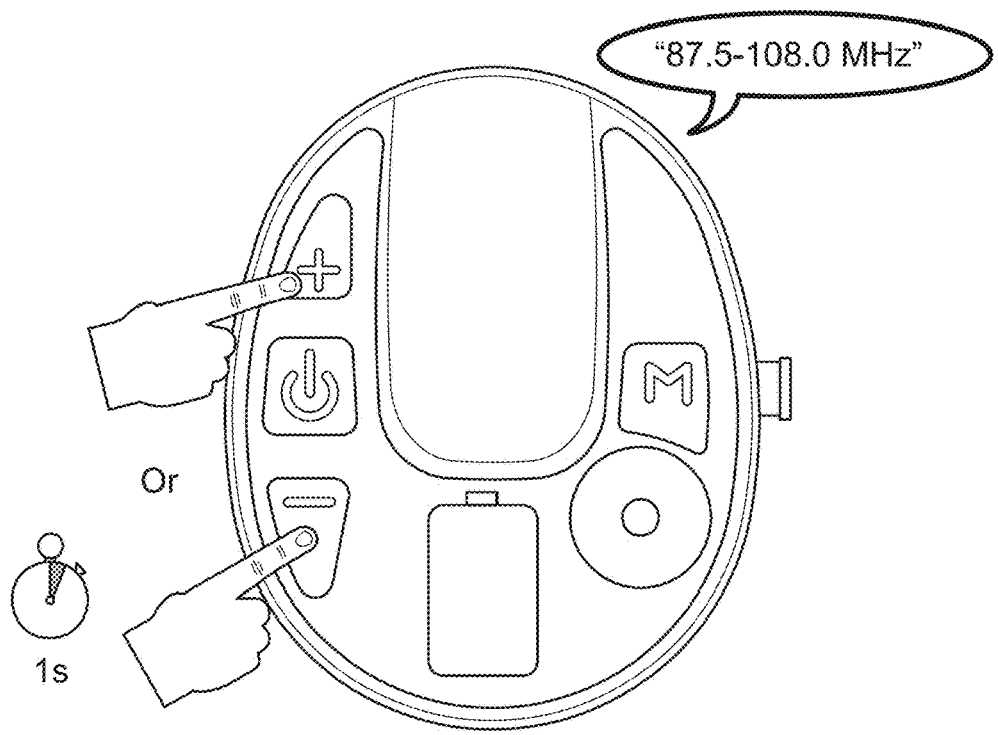
FIG. 5A illustrates a hearing protector with buttons for input selection in accordance with techniques of this disclosure.

FIG. 5A illustrates a hearing protector with buttons for input selection in accordance with techniques of this disclosure. This interface in FIG. 5A can pose a challenge to a user when changing from a low frequency (e.g. 87.5) to a high frequency (e.g. 108.0) as many button presses would be required to increment the frequency. A graphical user interface within the remote interface app to make this task more convenient for the user, as illustrated by a proposed graphical user interface in FIG. 5B.

Figure 5B:
FIG. 5B illustrates an example graphical user interface, in accordance with techniques of this disclosure.

FIG. 5B illustrates an example graphical user interface, in accordance with techniques of this disclosure. In FIG. 5B, the GUI proposed may enable a user to directly enter a radio station frequency using the numeric keyboard rather than sequentially incrementing through adjacent station frequencies. In some examples, a software user interface may also enable new functionality for a targeted piece of safety equipment. An example of adding new functionality can be seen in the same product scenario presented FIG. 5B. This example shows a Radio Preset functionality exposed within the remote interface GUI that allows saving and storing preset radio stations. This functionality is enabled solely through the remote interface and requires no modification to the existing safety equipment. Additionally, groupings of settings could configured into a single package and sent to the safety equipment in bulk, saving time when a user wishes to change multiple configuration settings In the case of Maintenance and Usage Data, digital communication between a remote interface and safety equipment can be used as previous concepts have demonstrated to change configuration and settings of the target safety equipment, but it can also be used to communicate data from the safety equipment to the remote interface, or even a cloud backend, for analysis and processing. In this scenario, the safety equipment would log usage information and upon periodic connection, transfer that data to the remote interface. Once the data is within the remote interface it could be viewed by the user through reports or other GUI elements, or transmitted to PPEMS 6 for further analysis and processing. This usage and performance data could be of particular value for warranty claims, repair centers or for guiding future product development efforts.

In the case of New Modes of Interaction, some existing safety equipment provides a single mode of interaction, via the tactile or button interfaces provided on the exterior of the equipment. Leveraging new capabilities available in smartphones and computing analysis, voice or motion commands could also be issued to the safety equipment via the remote interface. This may be useful for industrial environments where the user is typically preforming a manual task oftentimes involving both hands. In this scenario, a voice interface to control operation of the safety equipment could improve productivity and improve safety. A wide range of digitally enabled safety equipment may be designated for integration into the proposed remote interface, including but not limited to: Hearing Communication Equipment (Peltor WS ALERT XPI), Digital Self Retracting Line, Intrinsically Safe PAPR, Powered Air Purifying Respirator Connected System, Connected Welding Headtop, or any other connected PPE.

In some examples, techniques may include controlling and retrieving data from safety equipment. The proposed techniques may be directed to domain specific safety configurations for safety equipment as well as provide for advanced functionality (modes of interaction, usage data, component of a large safety data analysis system) that may not be addressed by conventional safety equipment.

Figure 6:
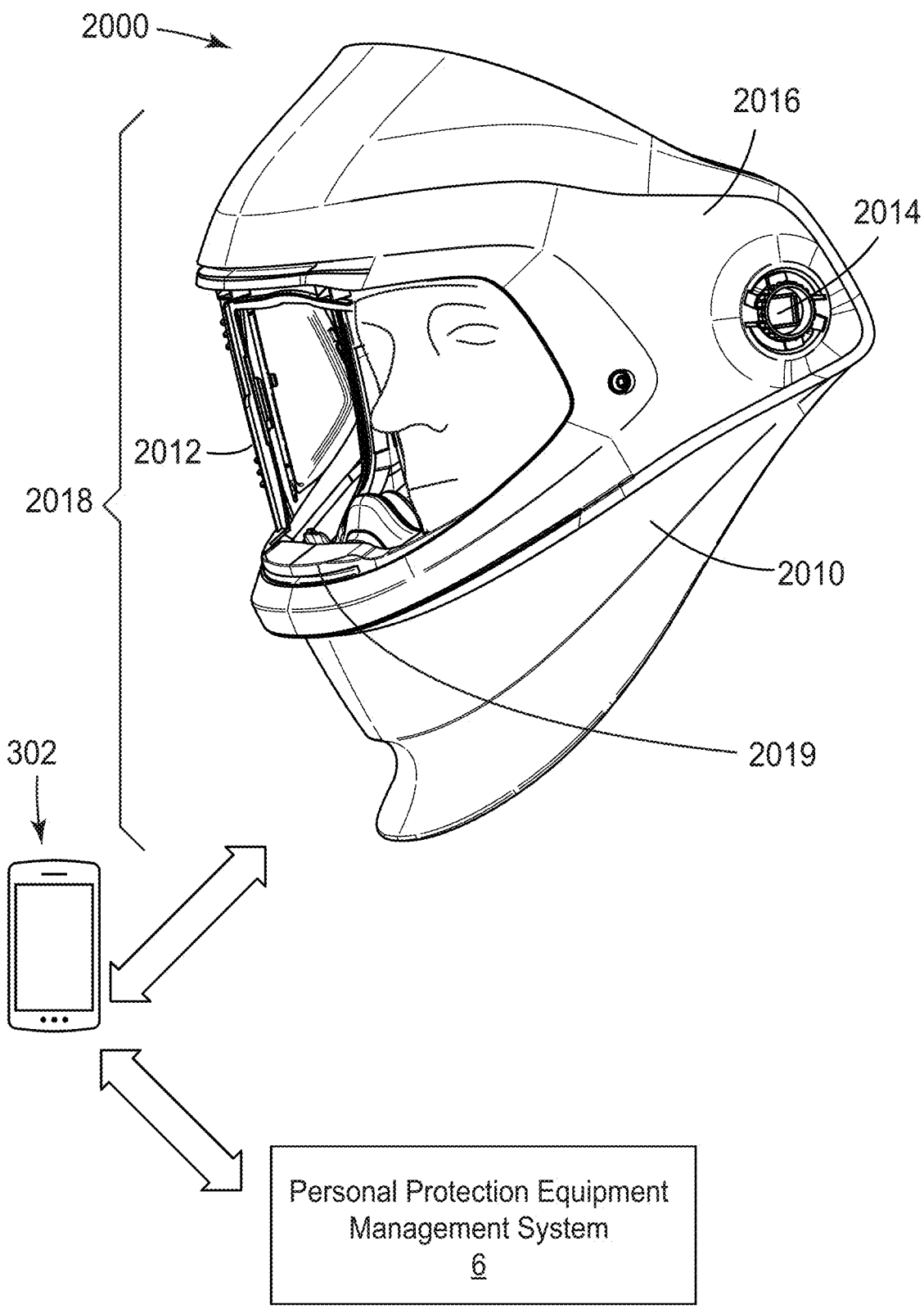
FIG. 6 illustrates a welding helmet with auto-darkening figure, in accordance with techniques of this disclosure.

FIG. 6 illustrates a welding helmet with auto-darkening figure, in accordance with techniques of this disclosure. FIG. 6 illustrates a system 2000 comprising head-mounted device 2010, visor attachment assembly 2014 that includes at least one position sensor coupled to the head-mounted device 2010, at least one visor 2016 that includes light-filtering shield coupled to the at least one position sensor; at least one light detector 2019; and at least one computing device 302 communicatively coupled to the at least one position sensor and at least one light detector 2019. Light detector 2019 is capable of detecting at least: "high" input that indicates the presence of high light intensity, "low" input that indicates the absence of high light intensity, a change from high to low input, and a change from low to high input. In some examples, light detector 2019 may also detect intermediate levels of light intensity. Light detector 2019 is also capable of communicating the detection of such high and low input and changes there between to the other components of system 2000. As such, when expressions are used in this disclosure such as detects high input, detects low input, detects a change from high input to low input, etc., it will be understood that such detection is by way of light detector 2019.

In some examples, light detector 2019 may detect different types of light where different types refer to different wavelengths. An example of a type of light may be laser light. In some examples, light detector 2019 may determine a type of light rather than an intensity of light. In other examples light detector 2019 may determine a type and an intensity of light.

In various embodiments, light detector 2019 may be located physically close to some or all of the other components (hardware, etc.) of system 2000 or may be located physically remote from some or all of the other components. Regardless, light detector 2019 may be in communication with other components of system 2000 via one or more wired or wireless communication channels as needed for functioning of system 2000. In one embodiment, light detector 2019 is capable of directly detecting incident light of high intensity (e.g., light detector 2019 comprises a photosensitive device, including but not limited to a photodiode, phototransistor, and so on). In this instance, "high input" means that light detector 2019 is directly sensing incident light of high intensity. (In such an embodiment, it may be preferential to locate light detector 2019 in close proximity to system 2000, so that the light incident on light detector 2019 is closely representative of the light incident on system 2000).

In an alternative embodiment, light detector 2019 is capable of detecting the high light intensity indirectly. In such a case a high input can comprise an input that is indicative of the presence of a high light intensity. In a particular embodiment, light detector 2019 is in communication with a (potentially) light-emitting device and is capable of receiving a high input from the light-emitting device that indicates that the light-emitting device is in a condition (e.g., powered up and operating) that is likely to emit high light intensity. In this context, a high input can comprise any signal sent via a connection (whether a dedicated wire, an optical fiber, a wireless connection, an IR signal, a radiofrequency broadcast, and the like) that can be received by light detector 2019 and that indicates that light-emitting device is in a condition that is likely to emit high light intensity. In such an arrangement, the light-emitting device may include a communication unit that is capable of performing such communication with light detector 2019 via a connection. If desired, such an arrangement can include a provision for two-way communication such that the light-emitting device can receive an acknowledgement from system 2000 or other computing device, prior to the light-emitting device emitting light.

FIG. 6 also illustrates computing device 302 comprising one or more computer processors and a memory comprising instructions that may be executed by the one or more computer processors. Computing device 302 may include the same, a subset, or a superset of functionality and components illustrated and described in other figures of this disclosure. Computing device 302 may be included in or attached to an article of personal protective equipment (e.g., system 2000), may be positioned on or attached to the worker in a separate device external to headtop 2010 and visor 2016, or may be in a remote computing device separate from the worker altogether (e.g., a remove server). Computing device 302 may perform any of the techniques with respect to an ADF or welding helmet or welding mask as described in this disclosure. Computing device 302 may communicate with PPEMS 6 in accordance with techniques of this disclosure.

In accordance with this disclosure, computing device 302 may receive, from light detector 2019, an indication that an intensity of light detected by the light detector exceeds an exposure threshold and/or that a type of light detected by the light detector matches a particular type of light. In some examples, the exposure threshold may be user-defined, hard-coded, or machine-generated. Computing device 302 may determine, from the position sensor included in visor attachment assembly 2014, that the light-filtering shield is or is not positioned at the face of a worker to filter light with the intensity that exceeds the exposure threshold and/or the type of light matches a particular type. In some examples, computing device 302 may determine that the light-filtering shield is or is not positioned at the face of a worker to filter light with the intensity that exceeds the exposure threshold within a threshold time at which the user was in a location during which the light exposure was present. As shown in FIG. 6, visor 2016 is positioned at the face of a worker to filter light with the intensity that exceeds the exposure threshold (e.g., active position). Visor 2016 may not be positioned at the face of a worker to filter light with the intensity that exceeds the exposure threshold (e.g., standby position).

Computing device 320 may generate, in response to the determination that the light-filtering shield is not positioned at the face of a worker to filter light with the intensity that exceeds the threshold and/or the type of light matches a particular type, an indication for output. In some examples, the indication of output may be haptic or audible and output at one or more computing devices as described in this disclosure. Computing device 320 may generate any type of indication of output. In some examples, the indication of output may be a message that includes various notification data. Notification data may include but is not limited to: an alert, warning, or information message; a type of personal protective equipment; a worker identifier; a timestamp of when the message was generated; a position of the personal protective equipment; one or more light intensities, or any other descriptive information. In some examples, the message may be sent to one or more computing devices as described in this disclosure and output for display at one or more user interfaces of output devices communicatively coupled to the respective computing devices. In some examples computing device 320 may receive an indication whether welding activity was occurring (e.g., welding arc was present) and generate the indication of output further based on whether the welding activity was occurring.

Figure 7:
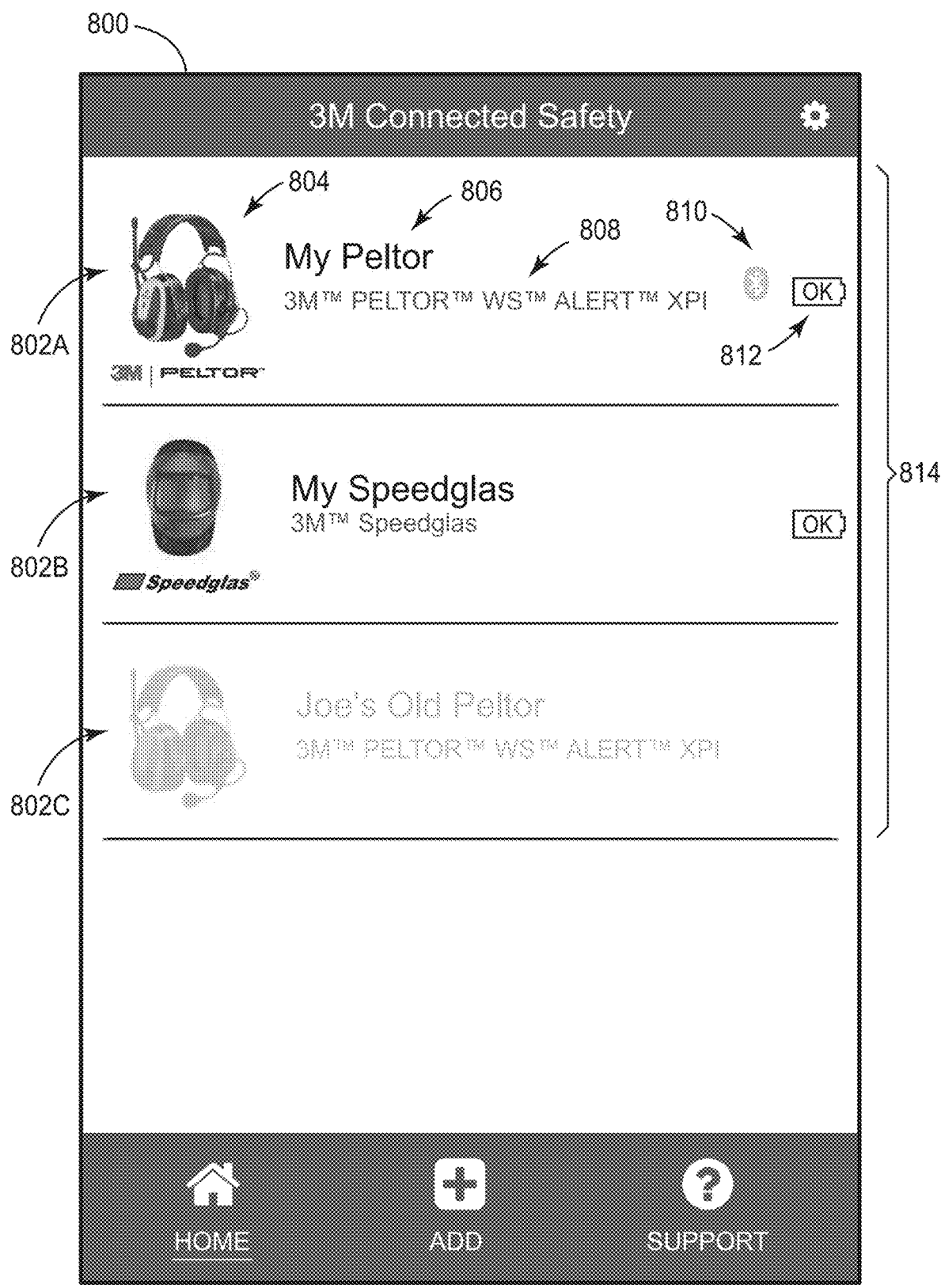
FIG. 7 illustrates a graphical user interface that indicates a set of PPE controlled by a particular user, in accordance with techniques of this disclosure.

FIG. 7 illustrates a graphical user interface that indicates a set of PPE controlled by a particular user, in accordance with techniques of this disclosure. Although FIG. 7 illustrates an example arrangement of graphical elements, other arrangements of graphical elements are possible and within the spirit and scope of this disclosure. Although FIG. 7 illustrates example appearances of graphical elements, other appearances of graphical elements are possible and within the spirit and scope of this disclosure.

In some examples a computing device, such as computing device 302 (as shown in FIG. 6) may output graphical user interface 800 for display. As shown in FIG. 7, graphical user interface 800 may include a set 814 of PPE graphical elements 802A-802C ("PPE graphical elements 802"). As such, computing device 302 may output for display, based at least in part on the data received from the at least one article of PPE, graphical user interface 800 that contemporaneously includes a set 814 of one or more graphical elements 800, wherein each respective graphical element corresponds to a respective article of PPE in the set of PPE. In some examples, at least one graphical element, e.g., 802A, in the set of one or more graphical elements indicates the particular type of the at least one article of PPE.

Each graphical element in graphical elements 802 may correspond to an article of PPE, which is connected, connectable, or was previously connected to computing device 302. In some examples, an appearance of a graphical element may indicate whether the PPE that corresponds to the graphical element is currently connected to computing device 302. For instance, the opacity level of graphical element 802C may indicate that the PPE that corresponds to graphical element 802C is not currently connected to computing device 302 and/or was previously connected to computing device 302.

Graphical element 802A, as an example, may include graphical content. For instance, graphical element 802A may include an image 804 of the PPE that corresponds to graphical element 802A. Graphical element 802A may include a user-defined label for the PPE that corresponds to graphical element 802A. Graphical element 802A may include pre-defined descriptive information for the PPE that corresponds to graphical element 802A. In some examples, pre-defined descriptive information may include a model, type, unique identifier, or any other suitable information. In some examples, the pre-defined descriptive information may be received from the PPE using a connection with computing device 302. In some examples, graphical element 802A may include one or more state indicators, such as connection status or connection type indicator, as illustrated by connection state indicator 810. In some examples, graphical element 802A may include battery state indicator 812. In still other examples, graphical element 802A may include a state indicator for expiration, use time, or remaining life of the PPE or a component of the PPE.

In some examples, the visual appearance of the state indicator may be varied based on one or more possible states for the state indicator. For instance, one or more states may be whether a connection exists between the PPE and computing device, whether the battery state is above or below a threshold battery life, whether the PPE or component of PPE is above or below a usage, expiration, or remaining life threshold, whether a fault at the PPE has occurred. The visual appearance may be varied based on color, size, shape, pattern, animation, or any other visual characteristic that may be modified.

In some examples, a graphical element, such as graphical element 802A may be selectable in response to a user input. For instance, if graphical element 802A is output for display at a touchscreen and a user touches the touchscreen at a location of the touchscreen that includes a portion of graphical element 802A, the computing device may perform one or more operations. For instance, a user may provide an input to select graphical element 802A, which causes computing device 302 to transition from display of the graphical user interface 800 to display of a graphical user interface that contemporaneously includes at least one identifier of the at least one article of PPE and a graphical element that indicates at least one time-based event. In other examples, a user may provide an input to select graphical element 802A, which causes computing device 302 to transition from display of the graphical user interface 800 to display of a graphical user interface that is different than graphical user interface 800. In some examples, the transition from graphical user interface 800 to a different graphical user interface may be a direct transition in which no other graphical user interface is output for display between the transition from graphical user interface 800 to a different graphical user interface. In other examples, the transition from graphical user interface 800 to a different graphical user interface may be an indirect transition in which at least one other graphical user interface is output for display between the transition from graphical user interface 800 to a different graphical user interface.

In some examples, computing device 302 receives sets of data from each of the different articles of PPE, wherein each set of data is based at least in part on a type of each of the different articles of PPE. Computing device 302 may generate for display a user interface that contemporaneously includes a plurality of graphical elements that are based at least in part on at least two sets of data that correspond to at least two different articles of PPE of the plurality of different articles of PPE. Computing device 302, in response to receiving an indication of user input that corresponds to at least one of the plurality of graphical elements, may perform at least one operation, as described in this disclosure. In some examples, an indication of user input that corresponds to at least one of the plurality of graphical elements comprises a configuration change to a current operation of the at least one of the plurality of graphical elements. In some examples, the configuration change corresponds to a first article of PPE, wherein the configuration change automatically causes another configuration change to a second article of PPE, the first and second articles of PPE each assigned to the particular user. In some examples, an indication of user input that corresponds to at least one of the plurality of graphical elements comprises a configuration change to a current operation of the at least one of the plurality of graphical elements. In some examples, the configuration change corresponds to a first article of PPE, wherein the configuration change automatically causes another configuration change to a second article of PPE, the first and second articles of PPE each assigned to the particular user.

In the present detailed description of the preferred embodiments, reference is made to the accompanying drawings, which illustrate specific embodiments in which the invention may be practiced. The illustrated embodiments are not intended to be exhaustive of all embodiments according to the invention. It is to be understood that other embodiments may be utilized and structural or logical changes may be made without departing from the scope of the present invention. The following detailed description, therefore, is not to be taken in a limiting sense, and the scope of the present invention is defined by the appended claims.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "proximate," "distal," "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above or on top of those other elements.

As used herein, when an element, component, or layer for example is described as forming a "coincident interface" with, or being "on," "connected to," "coupled with," "stacked on" or "in contact with" another element, component, or layer, it can be directly on, directly connected to, directly coupled with, directly stacked on, in direct contact with, or intervening elements, components or layers may be on, connected, coupled or in contact with the particular element, component, or layer, for example. When an element, component, or layer for example is referred to as being "directly on," "directly connected to," "directly coupled with," or "directly in contact with" another element, there are no intervening elements, components or layers for example. The techniques of this disclosure may be implemented in a wide variety of computer devices, such as servers, laptop computers, desktop computers, notebook computers, tablet computers, hand-held computers, smart phones, and the like. Any components, modules or units have been described to emphasize functional aspects and do not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset. Additionally, although a number of distinct modules have been described throughout this description, many of which perform unique functions, all the functions of all of the modules may be combined into a single module, or even split into further additional modules. The modules described herein are only exemplary and have been described as such for better ease of understanding.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor", as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the example, certain acts or events of any of the methods described herein can be performed in a different sequence, may be added, merged, or left out all together (e.g., not all described acts or events are necessary for the practice of the method). Moreover, in certain examples, acts or events may be performed concurrently, e.g., through multi-threaded processing, interrupt processing, or multiple processors, rather than sequentially.

In some examples, a computer-readable storage medium includes a non-transitory medium. The term "non-transitory" indicates, in some examples, that the storage medium is not embodied in a carrier wave or a propagated signal. In certain examples, a non-transitory storage medium stores data that can, over time, change (e.g., in RAM or cache).

Various examples have been described. These and other examples are within the scope of the following claims.

What is claimed is:

1. A system comprising:
a plurality of different articles of personal protection equipment (PPE) (13, 326, 328) that are all controlled by a particular user (10), wherein each respective article of PPE comprises a respective communication device (14);
a computing device (16, 302, 302) comprising:
a second communication device (306);
one or more computer processors (304); and
a memory (324, 318, 322) comprising instructions that when executed by the one or more computer processors cause the one or more computer processors to:
receive sets of data (314) from each of the different articles of PPE, wherein each set of data is based at least in part on a type of each of the different articles of PPE;
generate for display a user interface (800) that contemporaneously includes a plurality of graphical elements (814, 802) that are based at least in part on at least two sets of data that correspond to at least two different articles of PPE of the plurality of different articles of PPE;
in response to receiving an indication of user input that corresponds to at least one of the plurality of graphical elements, perform at least one operation;
receive an audio signal in response to sound generated by the particular user;

determine that the audio signal comprises a voice command to change a configuration associated with a particular article of PPE of the at least two different articles of PPE based at least in part on the information in the audio signal corresponds to a particular type of the particular article of PPE;

in response to the determination that the audio signal comprises the voice command to change the configuration associated with the particular article of PPE, generate a message comprising data to change the configuration associated with the particular article of PPE; and send the message to the particular article of PPE.

2. The system of claim 1, wherein the indication of user input that corresponds to at least one of the plurality of graphical elements comprises a configuration change to a current operation of the at least one of the plurality of graphical elements.

3. The system of claim 2, wherein the configuration change corresponds to a first article of PPE, wherein the configuration change automatically causes another configuration change to a second article of PPE, the first and second articles of PPE each assigned to the particular user.

4. The system of claim 1, wherein a particular article of PPE in the at least two different articles of PPE determines whether the particular article of PPE is within at least one of a threshold distance of the computing device or within wireless communication range of the computing device; and in response to determining that the particular article of PPE is not within at least one of a threshold distance of the computing device or within wireless communication range of the computing device, prevents operation of at least one functionality of the particular article of PPE.

5. The system of claim 2, wherein the particular article of PPE is an auto-darkening filter of a welding mask and the functionality of the particular article of PPE is auto-darkening functionality.

6. The system of claim 1, wherein a particular article of PPE in the at least two different articles of PPE performs an authentication challenge with the computing device; and in response to the particular article of PPE failing the authentication challenge, prevent operation at least one functionality of the particular article of PPE.

7. The system of claim 6, wherein the authentication challenge is based at least in part on a password entered by the particular user at the computing device for the particular article of PPE.

8. The system of claim 7, wherein the authentication challenge is based at least in part on a cryptochip included in the particular article of PPE or public key encryption between the particular article of PPE and the computing device.

9. The system of claim 1, wherein the memory comprises instructions that when executed by the one or more computer processors cause the one or more computer processors to:

determine that a particular article of PPE in the at least two different articles of PPE is within wireless communication range of the computing device;

determine, based at least in part on a GPS location of the computing device, that the computing device is within a predefined region; and determine, based at least in part the determination that the particular article of PPE is within wireless communication range of the computing device and the determination that the computing device is within a predefined region, that the particular article of PPE is authorized for use.

10. The system of claim 9, wherein the memory comprises instructions that when executed by the one or more computer processors cause the one or more computer processors to:

enable, based at least in part on the determination that the particular article of PPE is authorized for use, operation of at least one functionality of the particular article of PPE.

11. The system of claim 1, wherein the memory comprises instructions that when executed by the one or more computer processors cause the one or more computer processors to:

store a user identifier of the particular user in association with a PPE identifier of a particular article of PPE in the at least two different articles of PPE;

in response to detecting multiple different PPE within wireless range of the computing device, determine, based at least in part on the user identifier and the PPE identifier, that the computing device is assigned to the particular user and that the particular article of PPE is assigned to the particular user; and establish a connection, based on the determination that the computing device is assigned to the particular user and that the particular article of PPE is assigned to the particular user, between the computing device and the particular article of PPE.

12. The system of claim 1, wherein the memory comprises instructions that when executed by the one or more computer processors cause the one or more computer processors to:

output for display, in a visual map, a graphical indication of a location of a particular article of PPE in the at least two different articles of PPE.

13. The system of claim 12, wherein the memory comprises instructions that when executed by the one or more computer processors cause the one or more computer processors to:

determine a set of locations where the user has used the particular article of PPE; and output for display in the visual map, graphical indications of the respective set of locations where the user has used the particular article of PPE.

14. The system of claim 13, wherein one or more of the graphical indications of the respective set of locations where the user has used the particular article of PPE further indicate that the particular article of PPE was in use at the respective set of locations.

15. The system of claim 1, wherein the memory comprises instructions that when executed by the one or more computer processors cause the one or more computer processors to:

generate a message in response to a safety event;
determine a priority of the message; and
send, based at least in part on the priority of the message, the message to a particular article of PPE in the at least two different articles of PPE.

16. The system of claim 15, wherein the memory comprises instructions that when executed by the one or more computer processors cause the one or more computer processors to:

receive data that corresponds to the notification from a remote computing device.

17. The system of claim 16, wherein the message comprises configuration data that changes a configuration of the particular article of PPE.

18. The system of claim 1, wherein to perform the at least one operation, the memory comprises instructions that when executed by the one or more computer processors cause the one or more computer processors to:
   receive statistical data about a particular article of PPE in the at least two different articles of PPE; and
   output for display the statistical data about the particular article of PPE.

19. The system of claim 18, wherein the memory comprises instructions that when executed by the one or more computer processors cause the one or more computer processors to:
   determine at least one of productivity data or a safety data that corresponds to usage of the particular article of PPE by the user; and
   output for display the at least one of productivity data or safety data that is based on the statistical data.

20. The system of claim 1, wherein the memory comprises instructions that when executed by the one or more computer processors cause the one or more computer processors to:
   receive an indication of a gesture performed by the user;
   generate, based at least in part on the gesture, a set of messages that change configuration of each of the at least two different articles of PPE of the plurality of different articles of PPE; and
   send the respective messages to the at least two different articles of PPE.

21. A method comprising:
   receiving sets of data (314) from each different article of personal protection equipment (PPE) of a plurality of different articles of PPE (13, 326, 328) that are all controlled by a particular user (10), wherein each set of data is based at least in part on a type of each of the different articles of PPE;
   generating, by a computing device (16, 60, 302, 302) and for display, a user interface (310, 800) that contemporaneously includes a plurality of graphical elements (814, 802) that are based at least in part on at least two sets of data that correspond to at least two different articles of PPE of the plurality of different articles of PPE; and
   in response to receiving an indication of user input that corresponds to at least one of the plurality of graphical elements, performing at least one operation;
   receiving an audio signal in response to sound generated by the particular user;
   determining that the audio signal comprises a voice command to change a configuration associated with a particular article of PPE of the at least two different articles of PPE based at least in part on the information in the audio signal corresponds to a particular type of the particular article of PPE;
   in response to determining that the audio signal comprises the voice command to change the configuration associated with the particular article of PPE, generating a message comprising data to change the configuration associated with the particular article of PPE; and
   sending the message to the particular article of PPE.

* * * * *